US012673103B2

(12) United States Patent
Gindy et al.

(10) Patent No.: US 12,673,103 B2
(45) **Date of Patent: *Jul. 7, 2026**

(54) HPV VACCINE

(71) Applicant: Merck Sharp & Dohme LLC, Rahway, NJ (US)

(72) Inventors: Marian E. Gindy, Haledon, NJ (US); John P. Bilello, San Carlos, CA (US); Amy S. Espeseth, Chalfont, PA (US); Andrew J. Bett, Lansdale, PA (US); Tong-Ming Fu, Philadelphia, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 831 days.

This patent is subject to a terminal disclaimer.

(21) Appl. No.: 17/799,464

(22) PCT Filed: Feb. 9, 2021

(86) PCT No.: PCT/US2021/017157

§ 371 (c)(1),
(2) Date: Aug. 12, 2022

(87) PCT Pub. No.: WO2021/163002

PCT Pub. Date: Aug. 19, 2021

(65) Prior Publication Data

US 2023/0123584 A1 Apr. 20, 2023

Related U.S. Application Data

(60) Provisional application No. 62/976,673, filed on Feb. 14, 2020.

(51) Int. Cl.

| | |
|---|---|
| ***A61K 39/39*** | (2006.01) |
| ***A61K 39/12*** | (2006.01) |
| ***A61P 31/20*** | (2006.01) |
| ***C12N 7/00*** | (2006.01) |
| *A61K 39/00* | (2006.01) |

(52) U.S. Cl.

CPC .............. *A61K 39/39* (2013.01); *A61K 39/12* (2013.01); *A61P 31/20* (2018.01); *C12N 7/00* (2013.01); *A61K 2039/5258* (2013.01); *A61K 2039/545* (2013.01); *A61K 2039/55505* (2013.01); *A61K 2039/55555* (2013.01); *A61K 2039/55572* (2013.01); *C12N 2710/20023* (2013.01); *C12N 2710/20034* (2013.01); *C12N 2710/20071* (2013.01)

(58) Field of Classification Search

CPC ................ A61K 2039/70; A61K 39/12; A61K 2039/55555; A61K 2039/55572; A61K 2039/5258; A61P 31/20; C12N 2710/20023; C12N 2710/20034; C12N 2710/20071; C12N 7/00

See application file for complete search history.

(56) References Cited

U.S. PATENT DOCUMENTS

| | | | | |
|---|---|---|---|---|
| 5,208,036 | A | 5/1993 | Eppstein et al. | |
| 5,264,618 | A | 11/1993 | Felgner et al. | |
| 5,279,833 | A | 1/1994 | Rose | |
| 5,283,185 | A | 2/1994 | Epand et al. | |
| 5,437,951 | A | 8/1995 | Lowy et al. | |
| 5,820,870 | A | 10/1998 | Joyce et al. | |
| 6,599,508 | B1 | 7/2003 | Gissmann et al. | |
| 6,890,557 | B2 | 5/2005 | Huang et al. | |
| 7,250,170 | B2 | 7/2007 | Bryan et al. | |
| 7,276,243 | B2 | 10/2007 | Jansen et al. | |
| 7,482,428 | B2 | 1/2009 | Jansen et al. | |
| 7,498,036 | B2 | 3/2009 | Bryan et al. | |
| 7,700,103 | B2 | 4/2010 | Bryan et al. | |
| 7,709,010 | B2 | 5/2010 | Bryan et al. | |
| 7,744,892 | B2 | 6/2010 | Bryan et al. | |
| 7,976,848 | B2 | 7/2011 | Bryan et al. | |
| 8,952,955 | B2 | 2/2015 | Yokoyama et al. | |
| 9,669,097 | B2 | 6/2017 | Stanton et al. | |
| 10,493,143 | B2 | 12/2019 | Ciaramella et al. | |
| 11,638,754 | B2 * | 5/2023 | Bett ....................... | A61K 39/12 424/204.1 |
| 2003/0077829 | A1 | 4/2003 | MacLachlan | |
| 2005/0008689 | A1 | 1/2005 | Semple et al. | |
| 2006/0240554 | A1 | 10/2006 | Chen et al. | |
| 2008/0020058 | A1 | 1/2008 | Chen et al. | |
| 2008/0057080 | A1 | 3/2008 | Luke et al. | |

(Continued)

FOREIGN PATENT DOCUMENTS

| | | | |
|---|---|---|---|
| WO | 2006114312 | A2 | 11/2006 |
| WO | 2007068907 | A2 | 6/2007 |

(Continued)

OTHER PUBLICATIONS

Of Giannini et al. Vaccine, 2006, vol. 24 (33-34), pp. 5937-5948.*
Baylor, N. W., Aluminum salts in vaccines—US perspective, Vaccine, 2002, S18-S23, 20.
Bryan, Janine T., Developing an HPV vaccine to prevent cervical cancer and genital warts, Vaccine, 2007, 3001-3006, 25.
Chan, Chee Kai et al., Human Papillomavirus Infection and Cervical Cancer: Epidemiology, Screening, and Vaccination-Review of Current Perspectives, Journal of Oncology, 2019, 1-11, Article ID 3257939.

(Continued)

*Primary Examiner* — Bao Q Li
(74) *Attorney, Agent, or Firm* — Jonathan B. Fitzgerald; Emily K. Sauter

(57) ABSTRACT

The present disclosure provides, among other things, a pharmaceutical composition that includes a lipid nanoparticle adjuvant and an anti-human papillomavirus (HPV) comprising HPV virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82.

17 Claims, 6 Drawing Sheets

(56) References Cited

U.S. PATENT DOCUMENTS

| | | | |
|---|---|---|---|
| 2008/0085870 | A1 | 4/2008 | Hermanson et al. |
| 2009/0263407 | A1 | 10/2009 | Dande et al. |
| 2009/0285881 | A1 | 11/2009 | Dande et al. |
| 2010/0055168 | A1 | 3/2010 | Dande et al. |
| 2010/0055169 | A1 | 3/2010 | Dande et al. |
| 2010/0063135 | A1 | 3/2010 | Dande et al. |
| 2010/0076055 | A1 | 3/2010 | Dande et al. |
| 2010/0099738 | A1 | 4/2010 | Hansen et al. |
| 2010/0104629 | A1 | 4/2010 | Dande et al. |
| 2013/0017239 | A1 | 1/2013 | Petit et al. |
| 2016/0361411 | A1 | 12/2016 | Gindy et al. |
| 2018/0289792 | A1 | 10/2018 | Ciaramella et al. |
| 2018/0296662 | A1 | 10/2018 | Ciaramella et al. |

FOREIGN PATENT DOCUMENTS

| | | | |
|---|---|---|---|
| WO | 2008112125 | A1 | 9/2008 |
| WO | 2009132131 | A1 | 10/2009 |
| WO | 2010/021865 | A1 | 2/2010 |
| WO | 2010042877 | A1 | 4/2010 |
| WO | 2010105209 | A1 | 9/2010 |
| WO | 2010146740 | A1 | 12/2010 |
| WO | 2011022460 | A1 | 2/2011 |
| WO | 2011076807 | A2 | 6/2011 |
| WO | 2012040184 | A2 | 3/2012 |
| WO | 2012177970 | A1 | 12/2012 |
| WO | 2015130584 | A2 | 9/2015 |
| WO | 2017029360 | A1 | 2/2017 |
| WO | 2021163002 | A1 | 8/2021 |

OTHER PUBLICATIONS

Harper, Diane M. et al., Efficacy of a bivalent L1 virus-like particle vaccine in prevention of infection with human papillomavirus types 16 and 18 in young women: a randomised controlled trial, Lancet, 2004, 1757-1765, 364.

ISCOM from Encyclopedia of Immunology (Second Edition), published by 1998, pp. 1-10.

Kirii, Yasuyuki, et al., Human Papillomavirus Type 58 DNA Sequence, Virology, 1991, 424-427, 185.

Klein, J. et al., Analysis of Aluminum Hydroxyphosphate Vaccine Adjuvants by 27 Al MAS NMR, Journal of Pharmaceutical Sciences, 2000, 311-21, 89(3).

Li, Zhihai et al., Rational design of a triple-type human papillomavirus vaccine by compromising viral-type specificity, Nature, 2018, 1-15, 9:5360.

M.J. Caulfield et al., Effect of Alternative Aluminum Adjuvants on the Absorption, Human Vaccines, 2007, 139-146, 3.

McMurray, H.R. et al., Viruses and Cancer—Biology of human papillomaviruses, Int. J. Exp. Pathol., 2001, 15-33, 82(1).

Nygård, Mari et al., Evaluation of the Long-Term Anti-Human Papillomavirus 6 (HPV6), 11, 16, and 18 Immune Responses Generated by the Quadrivalent HPV Vaccine, Clinical and Vaccine Immunology, 2015, 943-948, 22(8).

Schiller, John T. et al., Developing HPV virus-like particle vaccines to prevent cervical cancer: a progress report, Journal of Clinical Virology, 2000, 67-74, 19.

Shi, L et al., Gardasil: Prophylactic Human Papillomavirus Vaccine Development—From Bench Top to Bed-side, Clinical Pharmacology and Therapeutics, 2007, 259-264, 81(2).

Villa, Luisa L. et al., Immunologic responses following administration of a vaccine targeting human papillomavirus Types 6, 11, 16, and 18, Vaccine, 2006, 5571-5583, 24.

* cited by examiner

HPV VACCINE

FIELD OF THE INVENTION

The present invention relates generally to the prevention of human papillomavirus (HPV) infection. More specifically, the invention relates to pharmaceutical compositions and formulations administered as a single-dose vaccine, which include virus-like particles (VLPs) of HPV and a lipid nanoparticle (LNP) adjuvant. The present disclosure provides, among other things, a single-dose vaccine composition that includes lipid nanoparticles and an human papillomavirus (HPV) vaccine, where a single administration of the vaccine composition provides a comparable or enhanced immune response in comparison to multiple administrations of the same HPV vaccine formulated (or same HPV vaccine administered) without an LNP adjuvant. Further provided are methods of using the disclosed compositions and formulations.

CROSS REFERENCE TO RELATED APPLICATIONS

This application is a § 371 National Phase Application of International Application No. PCT/US2021/017157, filed Feb. 9, 2021, which claims the benefit of priority to U.S.S.N. Provisional Application No. 62/976,673, filed Feb. 14, 2020, the disclosure of which is are hereby incorporated by reference in their entirety.

BACKGROUND

Human papillomaviruses (HPVs) are small, double-stranded DNA viruses that infect the skin and internal squamous mucosal epithelia of men and women. HPVs are classified based on their carcinogenic properties. HPVs include major (L1) and minor (L2) capsid proteins. Over 200 distinct HPV genotypes have been identified (Li et al., "Rational design of a triple-type human papillomavirus vaccine by compromising viral-type specificity," Nature, 9:5360 (2018)), many of which have been associated with pathologies ranging from benign proliferative warts to malignant carcinomas of the cervix (for review; see McMurray et al., Int. J. Exp. Pathol. 82 (1): 15-33 (2001)). Those labeled as "high-risk" include HPV types 16, 18, 31, 33, 35, 39, 45, 51, 52, 56, 58, 68, and 59. (Chan et al., "Human Papillomavirus Infection and Cervical Cancer: Epidemiology, Screening, and Vaccination—Review of Current Perspectives," Journal of Oncology, vol. 2019, Article ID 3257939, 11 pages, 2019.)

HPV is the primary etiological agent in cervical cancer, one of the most common cancer in women, as well as squamous cell carcinomas of the anus, tonsil, tongue, vulva, vagina, and penis. HPV16 and HPV18 are well known as the most virulent of the high-risk HPV types as they cause approximately 70% of all invasive cervical cancer in the world.

Papillomaviruses are small (50-60 mm diameter), nonenveloped, icosahedral DNA viruses that encode early (E1-E7) and late (L1-L2) genes. The L1 protein is the major capsid protein and has a molecular weight of 55-60 kDa. Expression of the L1 protein or a combination of the L1 and L2 proteins in yeast, insect cells, mammalian cells or bacteria leads to self-assembly of virus-like particles (VLPs) (for review, see Schiller and Roden, in Papillomavirus Reviews: Current Research on Papillomaviruses: Lacey, ed. Leeds, UK: Leeds Medical Information, pp 101-12 (1996)).

VLPs are morphologically similar to authentic virions and are capable of inducing high titres of neutralizing antibodies upon administration into animals or humans. Because VLPs do not contain the potentially oncogenic viral genome, they present a safe alternative to the use of live virus in HPV vaccine development (for review; see Schiller and Hidesheim, J Clin. Virol. 19:67-74 (2000)). For this reason, the L1 and L2 genes have been identified as immunological targets for the development of prophylactic and therapeutic vaccines for HPV infection and disease.

VLP-based vaccines have proven to be effective at inducing immune responses in human patients vaccinated with bivalent HPV 16 and 18 VLP-based vaccines (Harper et al. Lancet 364 (9447): 1757-65 (2004)), quadrivalent HPV 6, 11, 16, and 18 VLP-based vaccines (Villa et al. Vaccine 24:5571-5583 (2006)) and multi-valent HPV 6, 11, 16, 18, 31, 33, 45, 52 and 58 VLP-based vaccines. Three approved VLP-based vaccines against HPV are administered according to 2 or 3 dose regimens. CERVARIX'R: (GlaxoSmithKline Biologics, Rixensart, Belgium) is a bivalent vaccine protective against HPV 16 and 18. GARDASIL® and GARDASIL® 9 (Merck & Co., Inc., Kenilworth, NJ, USA) protect against two and seven additional HPV types, respectively, and prevent additional HPV-related anogenital diseases, including wart formation. The additional five high risk strains in GARDASIL® 9 over GARDASIL® increases protection against from about 70% to about 90% of anogenital malignancies. (Id., M. Nygard, et al., "Evaluation of the long-term anti-human papillomavirus 6 (HPV6), 11, 16, and 18 immune responses generated by the quadrivalent HPV vaccine," Clinical and Vaccine Immunology, vol. 22, no. 8, pp. 943-948, 2015.)

Though improving, worldwide HPV vaccination rates remain suboptimal. The worldwide coverage of HPV vaccination rates can be improved by reducing the number of healthcare practitioner visits required for the vaccination, increasing education on HPV disease prophylaxis, and alleviating the social stigma associated with vaccination. The proportion of adolescents in the Americas and in Europe completing a two dose vaccination series is estimated to be under 50%. Accordingly, it is desirable to improve HPV vaccination rates by generating immunity against HPV through a single administration that provides a comparable immune response to an existing 2-3 dose HPV vaccine.

It was surprisingly found that a single-injection of an LNP adjuvant combined with a HPV vaccine provided a comparable or enhanced initial anti-HPV immune response when compared to the standard multi-dose protocol of known aluminum adjuvant-containing multivalent HPV vaccine.

SUMMARY

The present invention provides a pharmaceutical composition comprising at least one type of VLPs from human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, a lipid nanoparticle (LNP) adjuvant, and a pharmaceutically acceptable carrier. In one aspect, the present invention also provides a pharmaceutical composition comprising an aluminum adjuvant and VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82, an LNP adjuvant, and a pharmaceutically acceptable carrier.

The present invention further provides a pharmaceutical composition comprising: (a) VLPs of at least one HPV type (HPV VLPs), wherein at least one type of HPV is selected from the group consisting of HPV types: 6, 11, 16, 18, 26, 31, 33, 35, 39, 45, 51, 52, 53, 55, 56, 58, 59, 66, 68, 73, and 82; and (b) about 1 μg to about 200 mg of an LNP adjuvant, where the HPV VLPs comprise recombinant L1 or recombinant L1+L2 protein of the at least one HPV: where the VLPs of any one of the at least one HPV type are present in a concentration of about 1 μg to about 100 μg per 0.5 mL of the pharmaceutical composition: where the total VLP concentration is between 1 μg and 2000 μg per 0.5 mL of pharmaceutical composition.

The present invention further provides a pharmaceutical composition comprising: (a) HPV VLPs of at least one HPV type, wherein at least one type of HPV is selected from the group consisting of HPV types: 6, 11, 16, 18, 26, 31, 33, 35, 39, 45, 51, 52, 53, 55, 56, 58, 59, 66, 68, 73, and 82: (b) about 100 μg to about 900 μg of an aluminum adjuvant; and (c) about 1 μg to about 200 mg of a lipid nanoparticle (LNP) adjuvant, where the HPV VLPs comprise recombinant L1 or recombinant L1+L2 protein of the at least one HPV: where the VLPs of any one of the at least one HPV type are present in a concentration of about 1 μg to about 100 μg per 0.5 mL of the pharmaceutical composition: wherein the total VLP concentration is between 1 μg and 2000 μg per 0.5 mL of pharmaceutical composition; and wherein the HPV VLPs are adsorbed onto the aluminum adjuvant.

The present invention further provides a single-dose vaccine composition that includes (a) a lipid nanoparticle (LNP) adjuvant, wherein the LNP adjuvant comprises one or more cationic lipids in the amount of about 30 mole % to about 65 mole %, one or more polymer-lipid conjugates in the amount of about 0).5 mole % to about 4.0 mole %, one or more phospholipids in the amount of about 5 mole % to about 30 mole %, cholesterol in the amount of about 10 mole % to about 40) mole %, (b) a HPV vaccine composition comprising VLPs at least one type of HPV selected from the group consisting of HPV types: 6, 11, 16, 18, 26, 31, 33, 35, 39, 45, 51, 52, 53, 55, 56, 58, 59, 66, 68, 73, and 82, or HPV VLPs of at least one type of HPV selected from the group consisting of HPV types 6, 11, 16, 18, 26, 31, 33, 35, 39, 45, 51, 52, 53, 55, 56, 58, 59, 66, 68, 73, and 82, wherein the single-dose vaccine composition provides an elevated or comparable anti-HPV immune response relative to multiple doses of the same composition formulated, or administered, without the LNP adjuvant.

The present invention also provides a method of inducing an immune response to an HPV in a human patient comprising administering to the patient a pharmaceutical composition comprising HPV VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82, an LNP adjuvant, a pharmaceutically acceptable carrier, and, optionally, an aluminum adjuvant.

The present invention also provides a method of inducing an immune response to an HPV in a human patient comprising administering to the patient pharmaceutical composition comprising: (a) HPV VLPs of at least one HPV type, wherein the at least one type of human papillomavirus (HPV) is selected from the group consisting of HPV types: 6, 11, 16, 18, 26, 31, 33, 35, 39, 45, 51, 52, 53, 55, 56, 58, 59, 66, 68, 73, and 82: (b) optionally, about 100 μg to about 900 μg of an aluminum adjuvant; and (c) about 1 μg to about 200 mg of a lipid nanoparticle (LNP) adjuvant, where the HPV VLPs comprise recombinant L1 or recombinant L1+L2 protein of the at least one HPV type: where the HPV VLPs of any one of the at least one HPV type are present in a concentration of about 1 μg to about 100 μg per 0.5 mL of the pharmaceutical composition: wherein the total VLP concentration is between 1 μg and 2000 μg per 0.5 mL of the pharmaceutical composition; and wherein the HPV VLPs are adsorbed onto the aluminum adjuvant when the aluminum adjuvant is present.

The present invention also provides a method of inducing an immune response to a an HPV in a human patient comprising administering to the patient a single-dose vaccine composition that includes (a) an LNP adjuvant, wherein the LNP adjuvant comprises one or more cationic lipids in the amount of about 30 mole % to about 65 mole %, one or more polymer-lipid conjugates in the amount of about 0.5 mole % to about 4.0 mole %, one or more phospholipids in the amount of about 5 mole % to about 30 mole %, cholesterol in the amount of about 10 mole % to about 40 mole %, (b) (i) an HPV vaccine composition comprising HPV VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82 or (ii) HPV VLPs of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, wherein the single-dose vaccine composition provides an elevated or comparable anti-HPV immune response relative to multiple doses of the same composition formulated, or administered, without the LNP adjuvant.

The present invention also provides a method of inducing an immune response to an HPV in a human patient comprising administering to the patient (a) a pharmaceutical composition comprising HPV VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82 and (b) an LNP adjuvant.

The present invention also provides a method of preventing infection of a human patient by an HPV comprising administering to the patient a pharmaceutical composition comprising HPV VLPs of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and, an LNP adjuvant, a pharmaceutically acceptable carrier, and, optionally, an aluminum adjuvant.

The present invention also provides a method of preventing infection of a human patient by an HPV comprising administering to the patient a pharmaceutical composition comprising: (a) HPV VLPs of at least one HPV type, wherein the at least one type of HPV is selected from the group consisting of HPV types: 6, 11, 16, 18, 26, 31, 33, 35, 39, 45, 51, 52, 53, 55, 56, 58, 59, 66, 68, 73, and 82: (b) optionally about 100 μg to about 900 μg of an aluminum adjuvant; and (c) about 1 μg to about 200 mg of a lipid nanoparticle (LNP) adjuvant, where the HPV VLPs comprise recombinant L1 or recombinant L1+L2 protein of the at least one HPV: where the VLPs of any one of the at least one HPV type are present in a concentration of about 1 μg to about 100 μg per 0.5 mL of the pharmaceutical composition: wherein the total VLP concentration is between 1 μg and 2000 μg per 0.5 mL of the pharmaceutical composition; and wherein the HPV VLPs are adsorbed onto the aluminum adjuvant when the aluminum adjuvant is present.

The present invention also provides a method of preventing infection of a human patient by an HPV comprising administering to the patient a single-dose vaccine composition that includes (a) an LNP adjuvant, wherein the adjuvant comprises one or more cationic lipids in the amount of about 30 mole % to about 65 mole %, one or more polymer-lipid conjugates in the amount of about 0.5 mole % to about 4.0 mole %, one or more phospholipids in the amount of about 5 mole % to about 30 mole %, cholesterol in the amount of about 10 mole % to about 40 mole %, (b) (i) an HPV vaccine composition comprising VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82 or (ii) HPV VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82, wherein the single-dose vaccine composition provides an elevated or comparable anti-HPV immune response relative to multiple doses of the same composition formulated, or administered, without the LNP adjuvant.

The present invention also provided a method of preventing infection of a human patient by an HPV comprising co-administering to the patient (a) a pharmaceutical composition comprising HPV VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82 and (b) an LNP adjuvant.

The present invention also provides a method of delivering a pharmaceutical composition that induces a neutralizing titer against an HPV antigen in a host including: administering a single-dose vaccine composition comprising: (a) an LNP adjuvant, and (b) (i) an HPV composition comprising VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82, or (ii) VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82 and, (c) optionally, an aluminum adjuvant, and inducing a neutralizing titer against an antigen in the host, where the single-dose vaccine composition provides enhanced or comparable neutralizing titers when compared to multiple doses of the same composition formulated, or administered, without the LNP adjuvant.

The present invention also provides a method of delivering a pharmaceutical composition that induces a neutralizing titer against an HPV antigen in a host including: co-administering (a) an LNP adjuvant, and (b) a composition comprising HPV VLPs of at least one type of HPV selected from the group consisting of HPV types: 6, 11, 16, 18, 26, 31, 33, 35, 39, 45, 51, 52, 53, 55, 56, 58, 59, 66, 68, 73, and 82, and inducing a neutralizing titer against the HPV antigen in the host, where a single co-administration of (a) and (b) provides enhanced or comparable neutralizing titers when compared to multiple doses of the same composition of (b) administered without the LNP adjuvant.

The present invention also provides a kit comprising an HPV vaccine composition and an LNP adjuvant.

Definitions

As used throughout the specification and in the appended claims, the singular forms "a," "an," and "the" include the plural reference unless the context clearly dictates otherwise.

As used throughout the specification and appended claims, the following definitions and abbreviations apply:

About: As used herein, the term "about," when used herein in reference to a value, refers to a value that is the same as or, in context, is similar to the referenced value. In general, those skilled in the art, familiar with the context, will appreciate the absolute amount and/or relative degree of difference encompassed by "about" in that context. For example, in some embodiments, the term "about" can encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referenced value.

Adjuvant: As used herein, the term "adjuvant" refers to a composition or compound that is capable of enhancing the immune response against an antigen of interest. Adjuvants are substances or combinations of substances that are used in conjunction with a vaccine antigen to enhance (e.g., increase, accelerate, prolong and/or possibly target) or modulate to a different type (e.g., switch a Th1 immune response to a Th2 response, or a humoral response to a cytotoxic T cell response) the specific immune response to the vaccine antigen in order to enhance the clinical effectiveness of the vaccine. In some embodiments, the adjuvant may modify (Th1/Th2) the immune response. In some embodiments, the adjuvant may boost the strength and longevity of the immune response. In some embodiments, the adjuvant may broaden the immune response to a concomitantly administered antigen. In some embodiments, the adjuvant may be capable of inducing strong antibody and T cell responses. In some embodiments, the adjuvant may be used to decrease the amount of antigen necessary to provoke the desired immune response and provide protection against the disease. In some embodiments, the adjuvant may be used to decrease the number of injections needed in a clinical regimen to induce a durable immune response and provide protection against the disease. Adjuvant containing formulations described herein may demonstrate enhancements in humoral and/or cellular immunogenicity of vaccine antigens, for example, subunit vaccine antigens. Adjuvants of the present invention are not used to deliver antigens, antibodies, APIs, or VLPs.

Administration: As used herein, the term "administration" refers to the act of providing an active agent, composition, or formulation to a subject. Exemplary routes of administration to the human body can be through the eyes (ophthalmic), mouth (oral), skin (transdermal), nose (nasal), lungs (inhalant), rectal, vaginal, oral mucosa (buccal), ear, by injection (e.g., intravenously (IV), subcutaneously, intratumorally, intraperitoneally, intramuscular (IM), intradermal (ID) etc.) and the like.

Agent: As used herein, the term "agent" refers to a particle, compound, molecule, or entity of any chemical class including, for example, a VLP, a small molecule, polypeptide (e.g., a protein), polynucleotide (e.g., a DNA polynucleotide or an RNA polynucleotide), saccharide, lipid, or a combination or complex thereof. In some embodiments, the term "agent" can refer to a compound, molecule, or entity that includes a polymer, or a plurality thereof.

Antibody: As used herein, the term "antibody" (or "Ab") refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, and chimeric antibodies.

Antigen: As used herein, the term "antigen" refers to any antigen that can generate one or more immune responses. The antigen may be a protein (including recombinant proteins), VLP, polypeptide, or peptide (including synthetic peptides). In certain embodiments, the antigen is a lipid or a carbohydrate (polysaccharide). In certain embodiments, the antigen is a protein extract, cell (including tumor cell), or tissue. The antigen may be one that generates a humoral and/or CTL immune response.

API: As used herein, the term "API" refers to an active pharmaceutical ingredient, e.g. HPV VLP, which is a component of the compositions or formulations disclosed herein that is biologically active (e.g. capable of inducing an appropriate immune response) and confers a therapeutic or prophylactic benefit to a person or animal in need thereof. As used herein, an API is a vaccine active ingredient.

Cationic lipid: As used herein, the term "cationic lipid" refers to a lipid species that carries a net positive charge at a selected pH, such as physiological pH. Those of skill in the art will appreciate that a cationic lipid can include, but are not limited to, U.S. Patent Application Publication Nos. US 2008/0085870, US 2008/0057080, US 2009/0263407, US 2009/0285881, US 2010/0055168, US 2010/0055169, US 2010/0063135, US 2010/0076055, US 2010/0099738, US 2010/0104629, US 2013/0017239, and US 2016/0361411, International Patent Application Publication Nos. WO2011/022460 A1: WO2012/040184, WO2011/076807, WO2010/021865, WO 2009/132131, WO2010/042877, WO2010/146740, WO2010/105209, and in U.S. Pat. Nos. 5,208,036, 5,264,618, 5,279,833, 5,283,185, 6,890,557, and 9,669,097.

Co-administration: As used herein, the term "co-administration" or "co-administering" refers to administration of an LNP adjuvant and a pharmaceutical formulation (e.g., an HPV vaccine) concurrently, i.e., simultaneously in time, or sequentially, i.e., administration of an HPV vaccine followed by administration of the LNP adjuvant (or vice versa). That is, after administration of the HPV vaccine (or LNP adjuvant), the LNP adjuvant (or HPV vaccine) can be administered substantially immediately after the HPV vaccine (or LNP adjuvant) or the LNP adjuvant (or the HPV vaccine) can be administered after an effective time period after the HPV vaccine (or LNP adjuvant): the effective time period is the amount of time period is generally within 1, 2, 3, 5, 10, 15, 20, 25, 30, 45, or 60 minutes.

Dose: As used herein, the term "dose" means a quantity of an agent, API, formulation, or pharmaceutical composition taken or recommended to be taken at a particular time.

Formulation: As used herein, the term "formulation" refers to a composition containing an active pharmaceutical or biological ingredient, along with one or more additional components. The term "formulation" is used interchangeably with "pharmaceutical composition." The formulations can be liquid or solid (e.g. lyophilized). Additional components that may be included as appropriate include pharmaceutically acceptable excipients, additives, diluents, buffers, sugars, amino acids, chelating agents, surfactants, polyols, bulking agents, stabilizers, lyo-protectants, solubilizers, emulsifiers, salts, adjuvants, tonicity enhancing agents, delivery vehicles, and anti-microbial preservatives. Formulations are nontoxic to recipients at the dosages and concentrations employed. In some embodiments, the formulation refers to a single-dose of vaccine, which can be included in any volume suitable for injection.

HPV and PV: As used herein, the terms "HPV" and "PV" refer to human papillomavirus and papillomavirus, respectively.

Lipid: As used herein, the term "lipid" refers to any of a group of organic compounds that are esters of fatty acids and are characterized by being insoluble in water or having low solubility in water but may be soluble in many organic solvents. Lipids can be divided in at least three classes: (1) "simple lipids," which include, e.g., fats and oils as well as waxes: (2) "compound lipids," which include, e.g., phospholipids and glycolipids; and (3) "derived lipids," which include, e.g., steroids.

Lipid nanoparticle: As used herein, the term "lipid nanoparticle" (or "LNP") refers to a lipid composition that forms a particle having a length or width measurement (e.g., a maximum length or width measurement) between 10 and 1000 nanometers. In some embodiments, the LNP may be used as an adjuvant to increase or enhance the immune response against an antigen of interest when used as a component of a vaccine. In some embodiments, a lipid nanoparticle can be used as an adjuvant or used in combination with non-LNP adjuvants.

MAA: As used herein, the term "MAA" (or Merck aluminum adjuvant) refers to an amorphous aluminum hydroxyphosphate sulfate adjuvant ("AAHS"). The term "MAA" is used interchangeably herein with the term "AAHS."

Multiple-dose: As used herein, the term "multiple-dose" refers to a vaccine composition, or pharmaceutical composition, that requires more than one dose or administration or injection of the components therein in a clinical regimen to induce a durable immune response and provide protection from a disease. One of skill in the art would understand how to determine a durable immune response, e.g., by measuring antibody titers over a specified period of time.

Neutral lipid: As used herein, the term "neutral lipid" refers to a lipid species that exists either in an uncharged or neutral zwitterionic form at a selected pH. At physiological pH, such lipids include, for example, diaeylphosphatidylcholine, diacylphosphatidyletbanolamine, ceramide, sphingomyelin, cephalin, cholesterol, cerebrosides and diacylglycerols.

Patient: As used herein, the term "patient" refers to any human being that is to receive the HPV vaccines, or pharmaceutical compositions, described herein. As defined herein, "patient" includes those already infected with HPV as well as those in which HPV infection is to be prevented.

Pharmaceutically acceptable: As used herein with respect to a carrier, diluent, or excipient of a pharmaceutical composition, the term "pharmaceutically acceptable" indicates that a carrier, diluent, or excipient must be compatible with the other ingredients of the composition and not deleterious to the recipient thereof.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue: parenteral administration, for example, by subcutaneous, intramuscular, intravenous or epidural injection as, for example, a sterile solution or suspension, or sustained-release formulation: topical application, for example, as a cream, ointment, or a controlled-release patch or spray applied to the skin, lungs, or oral cavity: intravaginally or intrarectally, for example, as a pessary, cream, or foam: sublingually: ocularly: transdermally: or nasally, pulmonary, and to other mucosal surfaces.

Single-dose: As used herein, the term "single-dose" refers to a vaccine composition that only requires one administration or injection in a clinical regimen to induce a durable immune response and provide protection from a disease. One of skill in the art would understand how to determine a durable immune response, e.g., by measuring antibody titers over a specified period of time.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutically Effective Amount: As used herein, the term "therapeutically effective amount" refers to an amount of the active ingredient (e.g. therapeutic protein, vaccine, or antibody) sufficient to produce the desired therapeutic effect in a human or animal, e.g. the amount necessary to elicit an immune response, treat, cure, prevent, or inhibit development and progression of a disease or the symptoms thereof and/or the amount necessary to ameliorate symptoms or cause regression of a disease. Therapeutically effective amount may vary depending on the structure and potency of the active ingredient and the contemplated mode of administration. One of skill in the art can readily determine a therapeutically effective amount of a given antibody or therapeutic protein or vaccine antigen.

Vaccine: As used herein, the term "vaccine" or "immunogenic composition" refers to a substance used to stimulate the production of antibodies and provide immunity against one or several diseases, prepared from the causative agent of a disease, its products, or a synthetic substitute, treated to act as an antigen without inducing the disease. A vaccine composition may include at least one antigen or HPV VLP in a pharmaceutically acceptable vehicle useful for inducing an immune response in a host. The vaccine composition is administered by doses and techniques known to those skilled in the pharmaceutical or veterinary fields, taking into account factors such as the age, sex, weight, species, and condition of the recipient animal and the route of administration.

Valent: As used herein, the term "valent" refers to the presence of a specified number of antigens in a molecule. For example, the terms bi-valent, bivalent, 2 valent, or 2-valent refers to two different antigens. Similarly, the terms quadrivalent, 4 valent, or 4-valent refers to four different antigens. 9 valent or 9-valent both refer to nine different antigens.

Virus Like Particles: As used herein, the term "virus like particles" or "VLPs" refers to agents that are morphologically similar to authentic virions or provide an arrayed display of an antigen and are capable of inducing high antibody neutralization ratings after administration in an animal. VLPs lack the viral genetic material of the authentic virions and are thus non-infectious.

DETAILED DESCRIPTION

Figure 1A:
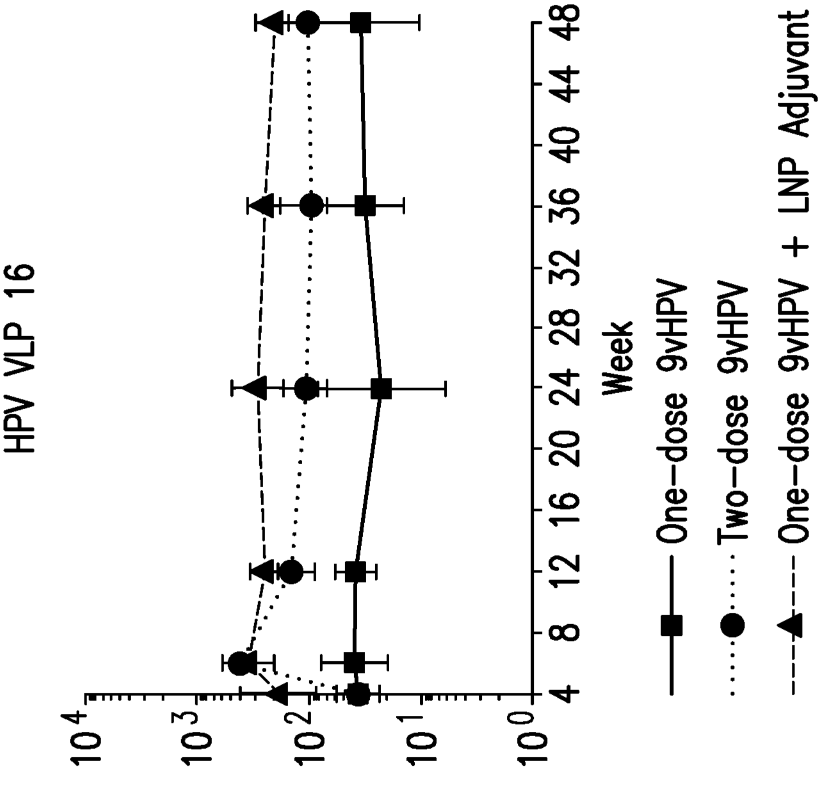
FIGS. 1A and 1B show the longitudinal HPV VLP 16 (FIG. 1A) and HPV VLP 18 (FIG. 1B) antibody levels in rabbits after a single inoculation of a 9 valent HPV vaccine combined with an LNP adjuvant.

Currently, there are multiple approved HPV vaccines that are composed of engineered virus like particles (VLPs) and are highly effective at protecting vaccinated patients against premalignant lesions and anogenital cancers and genital warts when administered prior to natural infection in subjects 9 years and older as multidose regimens. In accordance with this invention, it has been shown that a single-dose HPV vaccine composition that includes HPV VLPs of at least one HPV type ("targeted HPV types") and an LNP adjuvant are able to provide comparable or enhanced antibody titers to the same targeted HPV types when compared to multiple-doses of vaccine compositions that include VLPs of the targeted HPV types formulated, or administered, without an LNP adjuvant. The compositions of the present invention are intended to generate immunity against HPV subtypes through a single-injection regimen that is comparable to, at least, a 2-3 injection regimen of such HPV vaccine, including an approved two, four, or nine valent HPV vaccine.

The LNP Adjuvant

Lipid nanoparticle (LNP) adjuvants of the present invention are used herein to boost the immunological response of the HPV vaccine. Generally, LNP adjuvants of immunological compositions of the present invention include one or more cationic lipids, one or more polymer-lipid conjugates (e.g., a poly(ethylneglycol)-lipid (PEG-lipid)), one or more cholesterol, and one or more phospholipid.

In some embodiments, the LNP adjuvant includes any cationic lipid mentioned in U.S. Patent Application Publication Nos. US 2008/0085870, US 2008/0057080, US 2009/0263407, US 2009/0285881, US 2010/0055168, US 2010/0055169, US 2010/0063135, US 2010/0076055, US 2010/0099738, US 2010/0104629, US 2013/0017239, and US 2016/0361411, International Patent Application Publication Nos. WO2011/022460 A1: WO2012/040184, WO2011/076807, WO2010/021865, WO 2009/132131, WO2010/042877, WO2010/146740, WO2010/105209, and in U.S. Pat. Nos. 5,208,036, 5,264,618, 5,279,833, 5,283,185, 6,890,557, and 9,669,097.

In some embodiments, the LNP adjuvant may include a cationic lipid having the following structure, illustrated by Formula 1:

Formula 1

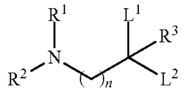

wherein:

$R^1$ and $R^2$ are each methyl:

$R^3$ is H:

n is 1 or 2:

L1 is selected from $C_8$-$C_{24}$ alkyl and $C_8$-$C_{24}$ alkenyl; and

L2 is selected from $C_4$-$C_9$ alkyl and $C_4$-$C_9$ alkenyl:

or any pharmaceutically acceptable salt or stereoisomer thereof.

In some embodiments, the cationic lipid is an aminoalkyl lipid. In some embodiments, the cationic lipid is an asymmetric aminoalkyl lipid. In some embodiments, the cationic lipid is (13Z, 16Z)-N, N-dimethyl-3-nonyldocosa 13, 16-dien-1-amine (See. U.S. Pat. No. 9,669,097).

In some embodiments, the LNP adjuvant includes 30-65 mole % cationic lipid. In some embodiments, the LNP adjuvant includes 30-55 mole % cationic lipid. In some embodiments, the LNP adjuvant includes 30-45 mole % cationic lipid. In some embodiments, the LNP adjuvant includes 55-65 mole % cationic lipid. In some embodiments, the LNP adjuvant includes 58 mole % cationic lipid.

In some embodiments, the LNP adjuvant may include a neutral lipid selected from: phospholipids, diaeylphosphatidylcholine, diacylphosphatidyletbanolamine, ceramide, sphingomyelin, cephalin, cholesterol, cerebrosides, diacylglycerols, and combinations thereof. In some embodiments, the neutral lipid may include a phospholipid and cholesterol.

In some embodiments, the neutral lipid may include a sterol, such as cholesterol. In some embodiments, the neutral lipid includes cholesterol. In some embodiments, the LNP adjuvant includes 10-40 mole % cholesterol. In some embodiments, the LNP adjuvant includes 15-25 mole % cholesterol. In some embodiments, the LNP adjuvant includes 10-20 mole % cholesterol. In some embodiments, the LNP includes 20-30 mole % cholesterol. In some embodiments, the LNP adjuvant includes 10-15 mole % cholesterol. In some embodiments, the LNP adjuvant includes 25-35 mole % cholesterol. In some embodiments, the LNP adjuvant includes 30 mole % cholesterol.

In some embodiments, the LNP adjuvant may include a phospholipid selected from: phospholipids, aminolipids and sphingolipids. In some embodiments, the LNP may include a phospholipid selected from: phosphatidylcholine, phosphatidylethanolamine, phosphatidylserine, phosphatidylinositol, phosphatidic acid, palmitoyloleryl phosphatidylcholine, lysophosphatidylcholine, lysophosphatidylethanolamine, dipalmitoylphosphatidylcholine, dioleoylphospbatidylcholine, dstearoylphosphatidylcholine or dilinoleoylphosphatidylcholine. In some embodiments, the LNP adjuvant may include a neutral lipid selected from: sphingolipid, glycosphingolipid families, diacylglycerols and S-acyloxyacids. In some embodiments, the LNP may include a neutral lipid selected from: phosphatidylcholine (PC), phosphatidylethanolamine (PE), and phosphatidylglycerol (PG), phosphatidylserine (PS), phosphatidylinositol (PI), phosphatidic acid (phosphatidate) (PA), dipalmitoylphosphatidylcholine, monoacyl-phosphatidylcholine (lyso PC), 1-palmitoyl-2-oleoyl-sn-glycero-3-phosphocholine (POPC), N-acyl-PE, phosphoinositides, and phosphosphingolipids. In some embodiments, the LNP may include a neutral lipid selected from: phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), and phosphatidylserine (DOPS). In some embodiments, the LNP may include a neutral lipid selected from: fatty acids include C14:0, palmitic acid (C16:0), stearic acid (C18:0), oleic acid (C18:1), linoleic acid (C18:2), linolenic acid (C18:3), arachidonic acid (C20:4), C20:0, C22:0 and lecithin. In some embodiments, the phospholipid may include 1,2-Distearoyl-sn-glycero-3-phosphocholine (DSPC).

In some embodiments, the neutral lipid may include a phospholipid. In some embodiments, the LNP adjuvant includes 5-30 mole % phospholipid. In some embodiments, the LNP adjuvant includes 5-15 mole % phospholipid. In some embodiments, the LNP includes 10-20 mole % phospholipid. In some embodiments, the LNP adjuvant includes 20-30 mole % phospholipid. In some embodiments, the LNP adjuvant includes 10-15 mole % phospholipid. In some embodiments, the LNP adjuvant includes 25-30 mole % phospholipid. In some embodiments, the LNP adjuvant includes 10 mole % phospholipid.

In some embodiments, the polymer-lipid conjugate may include a PEG-lipid. In some embodiments the PEG is conjugated to the lipid via a direct linkage (see, e.g., cPEG2000-DMG described below) or is conjugated to the lipid via linker (see, e.g., ePEG2000-DMG). In some embodiments, the PEG-lipid is conjugated to a diacylglycerol (a PEG-DAG). In some embodiments, the PEG is conjugated to DAG as described in, e.g., U.S. Patent Publication Nos. 2003/0077829 and 2005/008689. In one embodiment, the PEG-DAG conjugate is a PEG dimyristylglycerol (c14) conjugate. In some embodiments, the PEG-lipid is PEG-dimyristolglycerol (PEG-DMG).

In certain embodiments, the PEG-lipid is PEG conjugated to dimyristoylglycerol (PEG-DMG), e.g., as described in Abrams et al., 2010, Molecular Therapy 18 (1): 171, and U.S. Patent Application Publication Nos. US 2006/0240554 and US 2008/0020058.

In certain embodiments, the PEG-lipid comprises a polyethylene glycol having an average molecular weight raining of about 500 daltons to about 10,000 daltons, of about 75 daltoms to about 5,000 daltons, of about 1,000 daltons to about 5,000 daltons, of about 1,500 daltons to about 3,000 daltons or of about 2,000 daltons. In certain embodiments, the PEG-lipid comprises PEG1500, PEG2000 or PEG5000.

In some embodiments, the LNP adjuvant may include a PEG-lipid selected from:

1,2-Dimyristoyl-sn-glycerol methoxy-poly(ethylene glycol):

1,2-Dimyristoyl-sn-glycerol methoxy-poly(ethylene glycol)-2000 (cPEG2000-DMG(s)), which has the following structure:

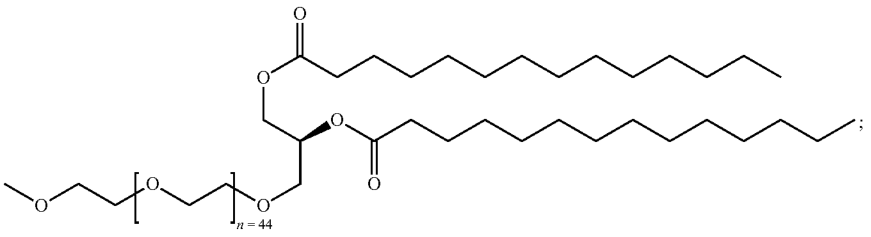

1,2-Dimyristoyl-rac-glycerol methoxy-poly(ethylene glycol);

1,2-Dimyristoyl-rac-glycerol methoxy-poly(ethylene glycol)-2000 (cPEG2000-DMG) which has the following structure:

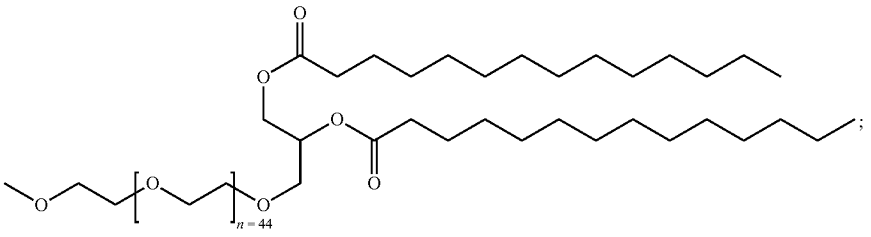

α-[8'-(1,2-Dimyristoyl-3-propanoxy)-carboxamide-3', 6'-Dioxaoctanyl]carbamoyl-ω-methyl-poly(ethylene glycol);

α-[8'-(1,2-Dimyristoyl-3-propanoxy)-carboxamide-3', 6'-Dioxaoctanyl]carbamoyl-ω-methyl-poly(ethylene glycol)-2000 (ePEG2000-DMG) which has the following structure:

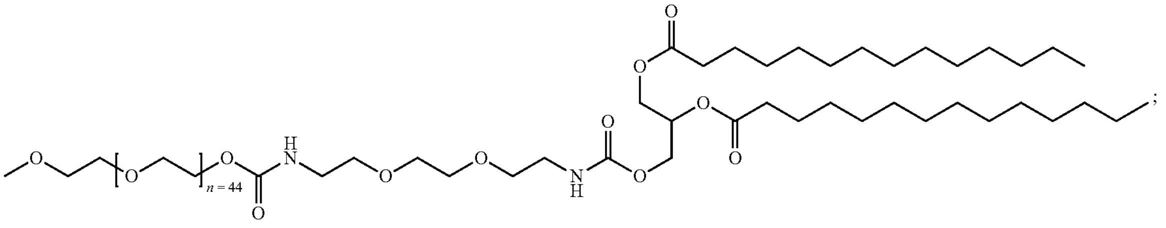

(R)-α-[8'-(1,2-Dimyristoyl-3-propanoxy)-carboxamide-3', 6'-Dioxaoctanyl]carbamoyl-ω-methyl-poly(ethylene glycol)-2000 which has the following structure:

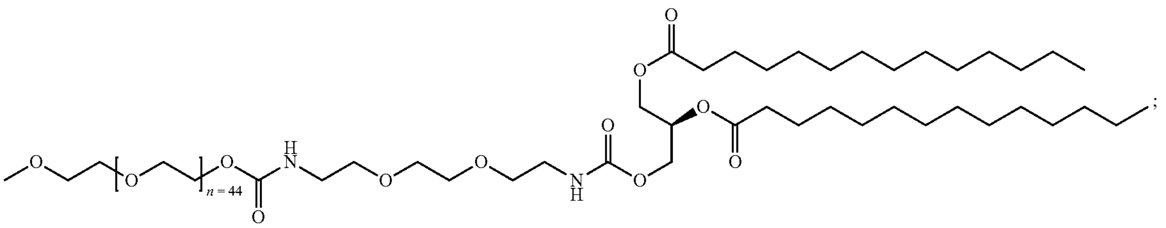

1,2-dimyristoyl-sn-glycero-3-phosphoethanolamine-N-[methoxy (polyethylene glycol);

1,2-dimyristoyl-sn-glycero-3-phosphoethanolamine-N-[methoxy (polyethylene glycol)-which has the following structure:

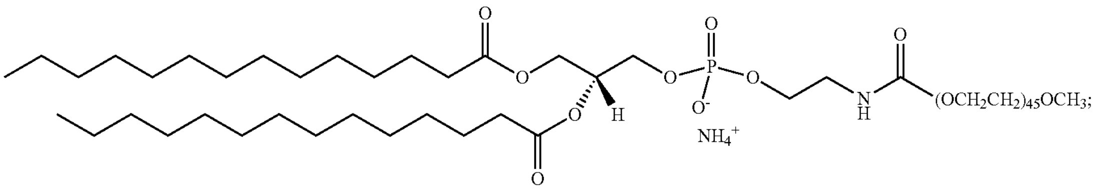

1,2-didecanoyl-rac-glycero-3-methylpolyoxyethylene;

1,2-didodecanoyl-rac-glycero-3-methylpolyoxyethylene; or 1,2-Distearoyl-rac-glycero-3-methylpolyoxyethylene.

In some embodiments, the LNP adjuvant includes 0.05-5 mole % polymer-lipid conjugate. In some embodiments, the LNP adjuvant includes 1~4 mole % polymer-lipid conjugate. In some embodiments, the LNP adjuvant includes 0.5-2 mole % polymer-lipid conjugate. In some embodiments, the LNP adjuvant includes 1~4 mole % polymer-lipid conjugate. In some embodiments, the LNP adjuvant includes 1-3 mole % polymer-lipid conjugate. In some embodiments, the LNP adjuvant includes 1-2.5 mole % polymer-lipid conjugate. In some embodiments, the LNP adjuvant includes 2 mole % polymer-lipid conjugate. (In each case, it is expressed as total mole % of lipid in the particle)

In some embodiments, the LNP adjuvant includes 30-65 mole % cationic lipid, 10-30 mole % cholesterol, 5-30 mole % phospholipid, and 0.05-4 mole % PEG-lipid. In some embodiments, the LNP adjuvant includes 55-65 mole % cationic lipid, 25-35 mole % cholesterol, 5-15 mole % phospholipid, and 1-2.5 mole % PEG-lipid. In some embodiments, the LNP adjuvant includes 40-50 mole % cationic lipid, 15-20 mole % cholesterol, 18-20 mole % phospholipid, and 1.5-2.5 mole % PEG-lipid. In some embodiments, the LNP adjuvant includes 56-59 mole % cationic lipid, 15-20 mole % cholesterol, 18-20 mole % phospholipid, and 0.5-1.5 mole % PEG-lipid. In some embodiments, the LNP adjuvant includes 56-59 mole % cationic lipid, 28-32 mole % cholesterol, 8-12 mole % phospholipid, and 1-3 mole % PEG-lipid. In some embodiments, the LNP adjuvant includes 58 mole % cationic lipid, 30 mole % cholesterol, 10 mole % PEG-lipid and 2 mole % PEG-lipid.

Methods of Making LNP Adjuvants

In some embodiments, the LNP adjuvants are formed, for example, by a rapid precipitation process that entails micromixing the lipid components dissolved in a lower alkanol solution (e.g. ethanol) with an aqueous solution using a confined volume mixing apparatus such as a confined volume T-mixer, a multi-inlet vortex mixer, microfluidics mixer devices, or other. The lipid solution may include one or more cationic lipids, one or more neutral lipid (e.g., phospholipids, DSPC, cholesterol), one or more polymer-lipid conjugate (e.g. cPEG2000-DMG, cPEG-2000-DMG(s) or ePEG2000-DMG) at specific molar ratios in ethanol.

In some embodiments, the aqueous and organic solutions are optionally heated to a temperature in the range of 25° C.-45° C., preferably 30° C.-40° C., and then mixed in a confined volume mixer to form the LNP. When a confined volume T-mixer is used, the T-mixer may have an internal diameter range from 0.25 to 10.0 mm. In some embodiments, the alcohol and aqueous solutions may be delivered to the inlet of the T-mixer using programmable syringe pumps, and with a total flow rate from 10 mL/min-600 L/minute. In some embodiments, the aqueous and alcohol solutions may be combined in the confined-volume mixer with a ratio in the range of 1:1 to 4:1 vol: vol. In some embodiments, the aqueous and alcohol solutions may be combined at a ratio in the range of 1.1:1 to 4:1, 1.2:1 to 4:1, 1.25:1 to 4:1, 1.3:1 to 4:1, 1.5:1 to 4:1, 1.6:1 to 4:1, 1.7:1 to 4:1, 1.8:1 to 4:1, 1.9:1 to 4:1, 2.0:1 to 4:1, 2.5:1 to 4:1, 3.0:1 to 4:1, and 3.5:1 to 4:1.

In some embodiments, the combination of ethanol volume fraction, solution flow rates, lipid(s) concentrations, mixer configuration and internal diameter, and mixer tubing internal diameter utilized at this mixing stage may provide LNPs having a particle size of the between 30 and 300 nm. The resulting LNP suspension may be diluted into higher pH buffers in the range of 6-8.

In some embodiments, the LNPs may also be concentrated and filtered via an ultrafiltration process to remove the alcohol. In some embodiments, the high pH buffer may also be removed and exchanged for a final buffer solution. In some embodiments, the final buffer solution may be selected from a phosphate buffered saline or any buffer system suitable for cryopreservation (for example, buffers containing sucrose, trehalose or combinations thereof). Following filtration, the vialed LNP product may be stored under suitable storage conditions (such as, 2° C.-8° C., or −80 to −20° C. if frozen) or may be lyophilized.

The VLPs

As stated above, the pharmaceutical compositions and formulations of the present invention comprise at least one HPV VLP type, such as HPV 16 or 18. In particular embodiments of the compositions disclosed herein, the vaccine further comprises VLPs of at least one additional HPV type. In further embodiments, the at least one additional HPV type is selected from the group consisting of: 6, 11, 16, 18, 26, 31, 33, 35, 39, 45, 51, 52, 53, 55, 56, 58, 59, 66, 68, 73, and 82. The pharmaceutical compositions of the present invention comprise HPV VLPs comprised of recombinant L1 or recombinant L1+L2 proteins of HPV. HPV L1 or L1+L2 protein can be expressed recombinantly by molecular cloning of L1 or L1+L2 DNA into an expression vector containing a suitable promoter and other appropriate transcription regulatory elements, and transferred into prokaryotic or eukaryotic host cells to produce recombinant protein. Techniques for such manipulations are fully described by Sambrook et al. (Molecular Cloning: A Laboratory Manual: Cold Spring Harbor Laboratory, Cold Spring Harbor, New York, (1989)), which is hereby incorporated by reference. VLPs can self-assemble when L1 protein is recombinantly expressed in a host cell.

The recombinant HPV L1 proteins of the present invention may be any full-length L1 protein sequence that can be found in nature or any mutated or truncated L1 protein that is capable of self-assembling into VLPs. In particular embodiments of the invention, the pharmaceutical compositions and vaccines described herein comprise HPV VLPs comprised of recombinant HPV L1 protein and do not contain HPV L protein. In certain embodiments, the vaccine compositions or pharmaceutical compositions described herein comprise HPV VLPs comprised of a full-length recombinant HPV L1 protein. L1 protein sequences for use in the present invention can be determined by isolating DNA from one or more clinical samples containing an HPV type of choice, determining the sequence of the HPV L1 DNA sequence, and translating the DNA sequence into an amino acid sequence using the genetic code. Many exemplary L1 sequences suitable for use in the present invention can be found in the literature. See, e.g., U.S. Pat. Nos. 5,820,870; 7,250,170; 7,276,243; 7,482,428:7,976,848:7,498,036; 7,700, 103:7,744,892; and 5,437,951: Kirii et al. (Virology 185 (1): 424-427 (1991)). Further L1 proteins that are useful in the compositions and formulations of the present invention include biologically active fragments and/or mutants of an HPV L1 sequence, including but not necessarily limited to amino acid substitutions, deletions, additions, amino terminal truncations and carboxy-terminal truncations, such that these mutations provide for L1 proteins or protein fragments that are capable of forming a VLP. See, e.g., International Publication WO 2006/114312 and U.S. Pat. No. 6,599,508. Appropriate host cells for the expression of recombinant HPV L1 or recombinant L1+L2 and subsequent self-assembly of VLPs include, but are not limited to yeast cells, insect cells, mammalian cells or bacteria. In exemplary embodiments of the invention, the VLPs are produced in yeast cells such as a yeast selected from the group consisting of: *Saccharomyces cerevisiae, Hansenula polymorpha, Pichia pastoris, Kluyvermyces fragilis, Kluveromyces lactis*, and *Schizosaccharomyces pombe*. In particular embodiments, the HPV VLPs are produced in *Saccharomyces cerevisiae* cells. Expression of HPV VLPs in yeast cells offers the advantages of being cost-effective and easily adapted to large-scale growth in fermenters.

The present invention also includes pharmaceutical compositions comprising mutant forms of HPV VLPs, such as HPV VLPs that comprise biologically active fragments and/or mutants of an HPV L1 or L2 protein, including but not necessarily limited to amino acid substitutions, deletions, additions, amino terminal truncations and carboxy-terminal truncations such that these mutations provide for proteins or protein fragments of therapeutic or prophylactic use and would be useful for HPV VLP vaccine development. Any such mutant form of an HPV L1 protein should be capable of forming VLPs and of provoking an immune response against the desired HPV type when administered to a human.

Additionally, one of skill in the art will recognize that the L1 or L1+L2 protein, which is used to self-assemble VLPs for inclusion in the compositions disclosed herein, may be encoded by a full-length wild-type HPV L1 or L2 polynucleotide, or may be encoded by a fragment or mutant of the known wild-type sequence. Wild-type polynucleotide sequences that encode mRNA expressing HPV L1 or L2 protein are available in the art. Any mutant polynucleotide will encode either a protein or protein fragment which at least substantially mimics the pharmacological properties of an HPV L1 or L2 protein, including the ability to form VLPs that are able to provoke an immune response against the HPV type of interest when administered to a human. Any such polynucleotide includes but is not necessarily limited to: nucleotide substitutions, deletions, additions, amino-terminal truncations and carboxy-terminal truncations.

The amount of virus-like particles of each HPV type to be included in the formulations and compositions of the present invention will depend on the immunogenicity of the expressed gene product. In general, a therapeutically effective dose of VLPs of any of the at least one HPV type is about 1 μg to about 100 μg. In some embodiments, a therapeutically effective dose of VLPs of any of the at least one HPV type is about preferably about 10 μg to 80 μg. In some embodiments, a therapeutically effective dose of VLPs of any of the at least one HPV type is about preferably about 20 μg to 60 μg.

In some embodiments, a 0.5 mL dose of a composition or vaccine including VLPs of the at least one HPV type includes:

15-40 μg of VLPs of HPV Type 6 L1 protein,
20-50 μg of VLPs of HPV Type 11 L1 protein,
30-70 μg of VLPs of HPV Type 16 L1 protein,
20-50 μg of VLPs of HPV Type 18 L1 protein,
10-30 μg of VLPs of HPV Type 31 L1 protein,
10-30 μg of VLPs of HPV Type 33 L1 protein,
10-30 μg of VLPs of HPV Type 45 L1 protein,
10-30 μg of VLPs of HPV Type 52 L1 protein,
10-30 μg of VLPs of HPV Type 58 L1 protein.

In some embodiments, a 0.5 mL dose of a composition or vaccine including VLPs of the at least one HPV type includes:

30 μg of VLPs of HPV Type 6 L1 protein,
40 μg of VLPs of HPV Type 11 L1 protein,
60 μg of VLPs of HPV Type 16 L1 protein,
40 μg of VLPs of HPV Type 18 L1 protein,
20 μg of VLPs of HPV Type 31 L1 protein,
20 μg of VLPs of HPV Type 33 L1 protein,
20 μg of VLPs of HPV Type 45 L1 protein,
20 μg of VLPs of HPV Type 52 L1 protein,
20 μg of VLPs of HPV Type 58 L1 protein.

The Aluminum Adjuvant

The aluminum adjuvant of the present invention may be in the form of aluminum hydroxide ($Al(OH)_3$), aluminum phosphate ($AlPO_4$), aluminum hydroxyphosphate, amorphous aluminum hydroxyphosphate sulfate (AAHS) or so-called "alum" ($KAl(SO_4)$-$12H_2O$) (see Klein et ah, Analysis of aluminum hydroxyphosphate vaccine adjuvants by (27) A1 MAS NMR., J Pharm. Sci. 89 (3): 311-21 (2000)). In exemplary embodiments of the invention provided herein, the aluminum adjuvant is aluminum hydroxyphosphate or AAHS. The ratio of phosphate to aluminum in the aluminum adjuvant can range from 0 to 1.3. In preferred embodiments of this aspect of the invention, the phosphate to aluminum ratio is within the range of 0.1 to 0.70. In particularly preferred embodiments, the phosphate to aluminum ratio is within the range of 0.2 to 0.50.

In some embodiments of the invention, the aluminum adjuvant is in the form of AAHS (referred to interchangeably herein as Merck aluminum adjuvant (MAA)). MAA carries zero charge at neutral pH, while AlOH carries a net positive charge and $AlPO_4$ typically carries a net negative charge at neutral pH. MAA has a higher capacity to bind HPV VLPs than AlOH. In addition, VLPs adsorbed to MAA can induce a greater humoral immune response in mice than VLPs adsorbed to AlOH. Caulfield et ah, Human Vaccines 3:139-146 (2007). While not wishing to be bound by theory, it is possible that net charge of the aluminum adjuvant can affect its ability to bind the VLP antigen, with strongly charged adjuvants unable to bind antigen as strongly as neutral charged adjuvants. For this reason, it is preferred that the aluminum adjuvant of the pharmaceutical compositions of the present invention have zero point surface charge at neutral pH. One of skill in the art will be able to vary the buffer, salt concentration and/or percent of free phosphate in order to allow a zero point surface charge at neutral pH.

One of skill in the art will be able to determine an optimal dosage of aluminum adjuvant that is both safe and effective at increasing the immune response to the targeted HPV type(s). For a discussion of the safety profile of aluminum, as well as amounts of aluminum included in FDA-licensed vaccines, see Baylor et al., Vaccine 20: S18-S23 (2002). Generally, an effective and safe dose of aluminum adjuvant varies from 100 to 900 μg/dose (200 to 1800 μg/mL concentration), in specific embodiments of the formulations and compositions of the present invention, there is between 200 and 300 μg aluminum adjuvant per dose of vaccine. In alternative embodiments of the formulations and compositions of the present invention, there is between 300 and 500 μg aluminum adjuvant per dose of vaccine.

The HPV VLP-Based Vaccine

Any HPV VLP-based vaccine is suitable for use in the pharmaceutical compositions and methods of the present invention. Known HPV VLP vaccines can be modified to include both an aluminum adjuvant and an LNP adjuvant. New vaccines can be developed according to the invention described herein that comprise at least one HPV type, optionally in the form of an HPV VLP adsorbed to an aluminum adjuvant, in combination with an LNP adjuvant. Additionally, new vaccines can be developed according to the invention described herein that comprise at least one HPV type in the form of an HPV VLP adsorbed to an aluminum adjuvant in combination with an LNP adjuvant.

One exemplary HPV vaccine is a bivalent vaccine protective against HPV 16 and 18, which is known commercially as CERVARIX® (GlaxoSmithKline Biologics, Rixensart, Belgium). Another exemplary HPV VLP vaccine is a non-infectious recombinant, quadrivalent vaccine prepared from highly purified VLPs of the major capsid (L1) protein of HPV types 6, 11, 16, and 18, and is referred to herein by its proprietary name GARDASIL® (Merck & Co., Inc., Kenilworth, NJ, USA), see Bryan, J.T. Vaccine 25 (16): 3001-6 (2007): Shi et al. Clinical Pharmacology and Therapeutics 81 (2): 259-64 (2007). Another exemplary HPV VLP vaccine is the nine-valent vaccine marketed for prevention of HPV (that includes the capsid (L1) protein of HPV types 6, 11, 16, 18, 31, 33, 45, 52, and 58), which is referred to herein by its proprietary name GARDASIL® 9 (Merck & Co., Inc., Kenilworth, NJ, USA).

In addition to VLPs, each GARDASIL® and GARDASIL® 9) vaccine dose may include an aluminum adjuvant (as amorphous aluminum hydroxyphosphate sulfate), sodium chloride, L-histidine, polysorbate 80, sodium borate, and water for injection. In some embodiments, the HPV vaccine may include 100-900 μg aluminum, 1-50 mg sodium chloride, 0.05-10 mg L-histidine, 1-100 μg polysorbate, 1-100 μg sodium borate, and water for injection. In some embodiments, the HPV vaccine may include about 500 μg aluminum, about 9.56 mg sodium chloride, about 0.78 mg L-histidine, about 50 μg polysorbate 80, about 35 μg sodium borate, and water for injection. Known HPV VLP vaccines can be modified to include both an aluminum adjuvant and an LNP adjuvant in accordance to the present invention.

In some embodiments of the invention, the pharmaceutical compositions and formulations comprise HPV VLP-based vaccines, or HPV VLPs as described herein, that are monovalent, bivalent, trivalent, and quadrivalent, 5-valent, 6-valent, 7-valent, 8-valent or 9-valent. In particular embodiments, the pharmaceutical compositions and formulations are 9-valent. In some embodiments, the pharmaceutical compositions comprise HPV VLP-based vaccines, or HPV VLPs as described herein, with more than four different types of HPV VLPs. For example, the pharmaceutical compositions and formulations of the present invention may include HPV VLP-based vaccines, or HPV VLPS as described herein, that are 8-valent, 9-valent, 10-valent, and so forth. For example, pharmaceutical compositions comprising VLPs of HPV 16 and/or HPV 18, without the inclusion of other HPV VLP types, are included within the scope of the invention. Multi-valent vaccines comprising different HPV VLPs than the HPV types included in GARDASIL® or GARDASIL® are also contemplated herein.

In some embodiments, VLPs of HPV types 6 and 11 are included in the pharmaceutical compositions, vaccines, and methods of the invention. In some embodiments, VLPs of HPV types 16, 31, and 35 are included. In some embodiments, VLPs of HPV types 18, 45, and 59 are included. In some embodiments, VLPs of HPV types 26, 51, and 69 are included. In some embodiments, VLPs of HPV types 33, 52, and 58 are included. In some embodiments, VLPs of HPV types 39, 68, and 70 are included. In some embodiments, VLPs of HPV types 53, 56, and 66 are included.

In some embodiments, the VLPs of HPV types 16 and 18 are included. In some embodiments, the VLPs of HPV types 6, 11, 16, and 18 are included. In some embodiments, the VLPs of HPV types 6, 11, 16, 18, 31, 33, 45, 52, and 58 are included. In some embodiments, the VLPs of HPV types 6, 11, 16, 18, 31, 33, 35, 45, 52, and 58 are included. In some embodiments, the VLPs of HPV types 6, 11, 16, 18, 31, 33, 35, 45, 52, 58, and 59 are included. In some embodiments, the VLPs of HPV types 6, 11, 16, 18, 26, 31, 33, 35, 45, 51, 52, 58, 59, and 69 are included. In some embodiments, the VLPs of HPV types 6, 11, 16, 18, 26, 31, 33, 35, 39, 45, 51, 52, 58, 59, 68, 69, and 70 are included. In some embodiments, the VLPs of HPV types 6, 11, 16, 18, 26, 31, 33, 35, 39, 45, 51, 52, 53, 56, 58, 59, 66, 68, 69, and 70 are included.

In some embodiments, the pharmaceutical compositions and formulations comprise HPV VLP-based vaccines and/or antigens as listed in Table I below:

TABLE I

| Name | Antigen | Adjuvant | Party |
|---|---|---|---|
| CERVARIX ® (2vHPV vaccine) | L1 VLP of HPV-16 and HPV-18 | Aluminum hydroxide and MPL | GlaxoSmithKline Biologics (Rixensart, Belgium) |
| GARDASIL ® (4vHPV vaccine) | L1 VLP of HPV-6, HPV-11, HPV-16 and HPV-18 | AHSS | Merck Sharp & Dohme Corp., Kenilworth NJ USA |

TABLE I-continued

| Name | Antigen | Adjuvant | Party |
|---|---|---|---|
| GARDASIL ® 9 (9vHPV vaccine) | L1 VLP of HPV-6, HPV-11, HPV-16, HPV-18, HPV-31, HPV-33, HPV-45, HPV-52 and HPV-58 | AHSS | Merck Sharp & Dohme Corp., Kenilworth NJ USA |
| CECOLIN ® | L1 VLP of HPV-16 and HPV-18 | Aluminum hydroxide | Xiamen Innovax |
| GEOCOLIN ® | L1 VLP of HPV-6 and HPV-11 | Aluminum hydroxide | Xiamen Innovax |
| L1 capsomers | L1 capsomers of HPV-16 | unknown | R. Garcea, University of Colorado-Boulder |
| RG1-VLP | HPV-16 L1-L2 (17-36) VLP | Aluminum hydroxide | R. Kirnbauer, NCI, Pathovax LLC |
| L2-AAV | L2 peptides of HPV-16 and HPV-31 displayed on AAV VLP | unknown | 2A Pharma |
| L2 multimer | Fusion protein of L2~11-88 of HPV-6, HPV-16, HPV-18, HPV-31 and HPV-39 | Alum | Sanofi, Bravo Vax |
| L2-thioredoxin | L2 peptide displayed on thioredoxin | unknown | M. Muller, DKFZ |
| AX03 | L2 peptide displayed on bacteriophage | unknown | Agilvax, NIAID |
| L1-E7 VLP | HPV-16 L1-E7 VLP | None | Medigene AG |
| TA-CIN | HPV-16 L2E7E6 fusion protein | None | Cantab Pharmaceuticals, Xenova |
| TA-GW | HPV-6 L2E7 fusion protein | Aluminum hydroxide or AS03 | Cantab Pharmaceuticals, GSK |

Single Dose Vaccine Compositions

In some embodiments, a single-dose vaccine composition is provided that is a pharmaceutical composition (i.e., includes a pharmaceutically acceptable carrier) and includes an LNP adjuvant and HPV VLP particles of at least one HPV type. In some embodiments, a single-dose vaccine composition is provided that includes an LNP adjuvant and HPV VLP particles of at least two HPV types. In some embodiments, a single-dose vaccine composition is provided that includes an LNP adjuvant and HPV VLP particles of at least four HPV types. In some embodiments, a vaccine composition is provided that includes an LNP adjuvant and HPV VLP particles of at least nine HPV types.

In some embodiments, a single-dose vaccine composition is provided that includes an LNP adjuvant and HPV VLP particles of at least one HPV type and an aluminum adjuvant. In some embodiments, a single-dose vaccine composition is provided that includes an LNP adjuvant and HPV VLP particles of at least two HPV types and an aluminum adjuvant. In some embodiments, a single-dose vaccine composition is provided that includes an LNP adjuvant and HPV VLP particles of at least four HPV types and an aluminum adjuvant. In some embodiments, a vaccine composition is provided that includes an LNP adjuvant and HPV VLP particles of at least nine HPV types and an aluminum adjuvant.

In some embodiments, a single-dose vaccine composition is provided that includes about 1 μg to about 200 mg LNP adjuvant, about 100 μg to about 900 μg aluminum adjuvant and HPV VLP particles of at least one HPV type, wherein teach of the HPV VLPs, when present in the single dose vaccine composition, are present in a concentration of about 1 μg to about 100 μg per 0.5 mL of the single-dose vaccine composition and wherein the total VLP concentration is between about 10 μg to about 2000 μg per 0.5 mL of the single-dose vaccine composition.

In some embodiments, a single-dose vaccine composition is provided that includes about 1 μg to about 200 mg LNP adjuvant, about 1 μg to about 2000 μg HPV VLP particles of at least two HPV types, and about 100 μg to about 900 μg aluminum adjuvant. In some embodiments, a single-dose vaccine composition is provided that includes an LNP adjuvant, HPV VLP particles of at least four HPV types, and about 100 μg to about 900 μg aluminum adjuvant. In some embodiments, a single-dose vaccine composition is provided that includes an LNP adjuvant, HPV VLP particles of at least nine HPV types and about 100 μg to about 900 μg aluminum adjuvant.

In some embodiments, a single-dose vaccine composition is provided that includes 1 μg to 200 mg LNP adjuvant and 1 μg to about 100 μg of each HPV VLPs present in the single dose vaccine composition. In some embodiments, a single-dose vaccine composition is provided that includes 1 μg to 200 mg LNP adjuvant and 2 μg to about 200 μg of HPV VLPs of two HPV types (i.e., the single-dose vaccine is a bivalent VLP HPV vaccine). In some embodiments, a single-dose vaccine composition is provided that includes 1 μg to 200 mg LNP adjuvant and 4 μg to about 400 μg of HPV VLPs of four HPV types (i.e., the single-dose vaccine is a quadrivalent VLP HPV vaccine). In some embodiments, single dose a vaccine composition is provided that includes 1 μg to 200 mg LNP adjuvant and 9 μg to about 900 μg of HPV VLPs of nine (9) HPV types (i.e., the single-dose vaccine is 9-valent VLP HPV vaccine). In some embodiments, a single dose vaccine composition is provided that includes 1 μg to 200 mg LNP adjuvant and 20 μg to about 2000 μg of HPV VLPs of twenty (20) HPV types (i.e., the single-dose vaccine is a 20-valen VLP HPV vaccine).

In some embodiments, a single-dose vaccine composition is provided that includes 1 μg to 200 mg LNP adjuvant, 1 μg to about 100 μg of a monovalent VLP HPV, and 100 μg to about 900 μg aluminum adjuvant. In some embodiments, a single-dose vaccine composition is provided that includes 1 μg to 200 mg LNP adjuvant and 1 μg to about 100 μg, per VLP, of a bivalent VLP HPV (i.e., HPV VLPs of two HPV types) and 100 μg to about 900 μg aluminum adjuvant. In some embodiments, a single-dose vaccine composition is provided that includes 1 μg to 200 mg LNP adjuvant and 1 μg to about 100 μg, per VLP, of a quadrivalent VLP HPV (i.e., HPV VLPS of four HPV types) and 100 μg to about 900 μg aluminum adjuvant. In some embodiments, a single-dose vaccine composition is provided that includes 1 μg to 200 mg LNP adjuvant and 1 μg to about 100 μg. per VLP, of a 9-valent VLP HPV (i.e., HPV VLPS of 9 HPV types) and 100 μg to about 900 μg aluminum adjuvant. In some embodiments, a single-dose vaccine composition is provided that includes 1 μg to 200 mg LNP adjuvant, 1 μg to about 100 μg, per VLP, of a 20-valent VLP HPV (i.e. HPV VLPS of 20 HPV types) and 100 μg to about 900 μg aluminum adjuvant.

In some embodiments, the single-dose vaccine composition includes 1 μg to about 100 μg, per VLP, of HPV VLPs (HPV types 16 and 18) and 1 μg to 200 mg of the LNP adjuvant, which is composed of (1) a cationic lipid, (2) cholesterol, (3) a phospholipid, DSPC, and (4) a polyethylene glycol lipid (e.g., cPEG2000-DMG, cPEG2000-DMG(s), or ePEG2000-DMG). In some embodiments, the single-dose vaccine composition includes 1 μg to about 100 μg, per VLP, of HPV VLPs (HPV types 6, 11, 16, and 18.) and 1 μg to 200 mg of the LNP adjuvant, which is composed of (1) a cationic lipid, (2) cholesterol, (3) a phospholipid, DSPC, and (4) a polyethylene glycol lipid (e.g., cPEG2000-DMG, cPEG2000-DMG(s), or ePEG2000-DMG). In some embodiments, the single-dose vaccine composition includes 1 μg to about 100 μg, per VLP, of HPV VLPs (HPV types 6, 11, 16, 18, 31, 33, 45, 52, and 58) and 1 μg to 200 mg of the LNP adjuvant, which is composed of (1) a cationic lipid. (2) cholesterol, (3) a phospholipid, DSPC, and (4) a polyethylene glycol lipid (e.g., cPEG2000-DMG, cPEG2000-DMG(s), or ePEG2000-DMG).

In some embodiments, the single-dose vaccine composition includes 1 μg to about 100 μg. per VLP, of HPV VLPs (HPV types 16 and 18), 100 μg to about 900 μg of an aluminum adjuvant, and 1 μg to 200 mg of the LNP adjuvant, which is composed of (1) a cationic lipid, (2) cholesterol, (3) a phospholipid, DSPC, and (4) a polyethylene glycol lipid (e.g., cPEG2000-DMG, cPEG2000-DMG(s), or ePEG2000-DMG). In some embodiments, the single-dose vaccine composition includes 1 μg to about 100 μg. per VLP, of HPV VLPs (HPV types 6, 11, 16, and 18.), 100 μg to about 900 μg of an aluminum adjuvant, and 1 μg to 200 mg of the LNP adjuvant, which is composed of (1) a cationic lipid, (2) cholesterol, (3) a phospholipid, DSPC, and (4) a polyethylene glycol lipid (e.g., cPEG2000-DMG, cPEG2000-DMG(s), or ePEG2000-DMG). In some embodiments, the single-dose vaccine composition includes 1 μg to about 100 μg, per VLP, of HPV VLPs (HPV types 6, 11, 16, 18, 31, 33, 45, 52, and 58), 100 μg to about 900 μg of an aluminum adjuvant, and 1 μg to 200 mg of the LNP adjuvant, which is composed of (1) a cationic lipid, (2) cholesterol, (3) a phospholipid, DSPC, and (4) a polyethylene glycol lipid (e.g., cPEG2000-DMG, cPEG2000-DMG(s), or ePEG2000-DMG).

The vaccines of the invention comprise VLPs containing the antigenic determinants required to induce the generation of neutralizing antibodies in the host. The vaccines are sufficiently safe to be administered without the risk of clinical infection, have no toxic side effects, are stable, compatible with conventional carriers and can be administered effectively. In some embodiments, LNP adjuvant of the present invention may be combined with a Human Papillomavirus Bivalent (Types 16 and 18) Vaccine, Recombinant. In some embodiments, LNP adjuvant of the present invention may be combined with CERVARIX®. In some embodiments, LNP adjuvant of the present invention may be combined with a Human Papillomavirus Quadrivalent (Types 6, 11, 16, 18) Vaccine, Recombinant. In some embodiments, LNP adjuvant of the present invention may be combined with GARDASIL®. In some embodiments, LNP adjuvant of the present invention may be combined with a Human Papillomavirus 9-valent Vaccine, Recombinant. In some embodiments, LNP adjuvant of the present invention may be combined with GARDASIL® 9.

Pharmaceutical compositions, formulations, and single-dose vaccines of the present invention may be administered subcutaneously, topically, orally, on the mucosa, intravenously, or intramuscularly. The pharmaceutical compositions, formulations, and vaccines are administered in an amount sufficient to elicit a protective response. Vaccines, pharmaceutical compositions and formulations can be administered by various routes, for example, orally, parenterally, subcutaneously, on the mucosa, or intramuscularly. The dose administered may vary depending on the general condition, sex, weight and age of the patient, the route of administration and the type of HPV VLP in the vaccine. The vaccine, pharmaceutical composition, for formulation may be in the form of a capsule, suspension, elixir or solution. It may be formulated with an immunologically acceptable carrier.

Kits of the Invention

Also provided herein are kits including any of the pharmaceutical compositions of single dose vaccines as described above and instructions for use.

Also provided herein are kits including (a) a pharmaceutical composition comprising HPV VLPs of at least one type of HPV and (b) an LNP adjuvant.

In some embodiments of the kits, the pharmaceutical composition of (a) comprises HPV VLPs comprising at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82. In some embodiment, the pharmaceutical composition of (a) is an HPV vaccine. In some embodiments, the HPV vaccine is a Human Papillomavirus Bivalent (Types 16 and 18) Vaccine, Recombinant. In some embodiments, the HPV vaccine is CERVARIX®. In some embodiments, the HPV vaccine is a Human Papillomavirus Quadrivalent (Types 6, 11, 16, 18) Vaccine, Recombinant. In some embodiments, the HPV vaccine is GARDASIL®. In some embodiments, the HPV vaccine is a Papillomavirus 9-valent Vaccine, Recombinant. In some embodiments, the HPV vaccine is GARDASIL® 9.

In some embodiments of the kits, the LNP adjuvant is any of the LNP adjuvants described herein above. In some embodiments, the kit includes 1 μg to 200 mg of an LNP adjuvant. In some embodiments, the LNP adjuvant is composed of (1) a cationic lipid, (2) cholesterol, (3) a phospholipid, (e.g., DSPC), and (4) a polyethylene glycol lipid (e.g., cPEG2000-DMG, cPEG2000-DMG(s), or ePEG2000-DMG). In some embodiments, the LNP adjuvant includes 30-65 mole % cationic lipid, 10-30 mole % cholesterol, 5-30 mole % phospholipid, and 0.05-4 mole % PEG-lipid. In some embodiments, the LNP adjuvant includes 55-65 mole % cationic lipid, 25-35 mole % cholesterol, 5-15 mole % phospholipid, and 1-2.5 mole % PEG-lipid. In some embodiments, the LNP adjuvant includes 40-50 mole % cationic lipid, 15-20 mole % cholesterol, 18-20 mole % phospholipid, and 1.5-2.5 mole % PEG-lipid. In some embodiments, the LNP adjuvant includes 56-59 mole % cationic lipid, 15-20 mole % cholesterol, 18-20 mole % phospholipid, and 0.5-1.5 mole % PEG-lipid. In some embodiments, the LNP adjuvant includes 58 mole % cationic lipid, 30 mole % cholesterol, 10 mole % PEG-lipid and 2 mole % PEG-lipid.

In some embodiments of the kits, the kit includes a label or packaging insert that includes a description of the components and/or instructions for use in vivo of the components therein. In some embodiments, the kits include instructions for co-administering (or vaccinating) the (a) pharmaceutical composition or HPV Vaccine and (b) the LNP adjuvant. In some embodiments, the kits include instructions for admixing the (a) pharmaceutical composition or HPV vaccine and (b) the LNP adjuvant and subsequentially administering (or vaccinating) the admixture toa patient.

In embodiment 1, a pharmaceutical composition is provided that comprises virus-like particles (VLPs) of at least one type of human papillomavirus (HPV) (HPV VLPs) selected from the group consisting of HPV types: 6, 11, 16, 18, 26, 31, 33, 35, 39, 45, 51, 52, 53, 55, 56, 58, 59, 66, 68, 73, and 82, a lipid nanoparticle (LNP) adjuvant, and a pharmaceutically acceptable carrier.

In embodiment 2, the pharmaceutical composition of embodiment 1 is provided, wherein the pharmaceutical composition comprises VLPs of at least HPV types 16 and 18.

In embodiment 3, the pharmaceutical composition of embodiments 1-2 is provided, wherein the pharmaceutical composition comprises VLPs of at least HPV types 6, 11, 16, and 18.

In embodiment 4, the pharmaceutical composition of embodiments 1-3 is provided, wherein the pharmaceutical composition comprises VLPs of at least HPV types 31, 45, 52, and 58.

In embodiment 5, the pharmaceutical composition of any of embodiments 1~4 is provided, wherein the pharmaceutical composition comprises VLPs of at least HPV types 6, 11, 16, 18, 31, 33, 45, 52, and 58.

In embodiment 6, the pharmaceutical composition of any of embodiments 1-5 is provided, wherein the LNP adjuvant comprises a cationic lipid, a phospholipid, cholesterol, and a PEG-lipid.

In embodiment 7, the pharmaceutical composition of any of embodiments 1-6 is provided, wherein the LNP adjuvant comprises 30-65 mole % cationic lipid, 5-30 mole % phospholipid, 10-40% cholesterol, and 0.5-4 mole % PEG-lipid.

In embodiment 8, the pharmaceutical composition of any of embodiments 1-7 is provided, wherein the LNP adjuvant comprises 55-65 mole % cationic lipid, 5-15 mole % phospholipid, 25-35% cholesterol, and 1-2.5 mole % PEG-lipid.

In embodiment 9, the pharmaceutical composition of any of embodiments 1-8 is provided, wherein the LNP adjuvant comprises DSPC, cholesterol, ePEG2000-DMG, and (13Z, 16Z)-N, N-dimethyl-3-nonyldocosa 13, 16-dien-1-amine.

In embodiment 10, the pharmaceutical composition of any of embodiments 1-9 is provided, wherein the LNP adjuvant comprises 5-15 mole % DSPC, 25-35 mole % cholesterol, 1-2.5 mole % ePEG2000-DMG, and 55-65 mole % (13Z, 16Z)-N, N-dimethyl-3-nonyldocosa 13, 16-dien-1-amine.

In embodiment 11, the pharmaceutical composition of any of embodiments 1-10 is provided, further comprising an aluminum adjuvant.

In embodiment 12, a pharmaceutical composition is provided comprising:

(a) virus-like particles (VLPs) at least one type of human papillomavirus (HPV) (HPV VLPs), wherein the at least one type of HPV is selected from the group consisting of HPV types: 6, 11, 16, 18, 26, 31, 33, 35, 39, 45, 51, 52, 53, 55, 56, 58, 59, 66, 68, 73, and 82;

(b) about 100 μg to about 900 μg of an aluminum adjuvant; and (c) about 1 μg to about 200 mg of a lipid nanoparticle (LNP) adjuvant, wherein each of the HPV VLPs comprise recombinant L1 or recombinant L1+L2 protein:

wherein each of the HPV VLPs, when present in the pharmaceutical composition, are present in a concentration of about 1 μg to about 100 μg per 0.5 mL of pharmaceutical composition;

wherein the total VLP concentration is between 1 μg and 2000 μg per 0.5 mL of pharmaceutical composition; and wherein the HPV VLPs are adsorbed onto the aluminum adjuvant.

In embodiment 13, the pharmaceutical composition of embodiment 12 is provided, wherein the pharmaceutical composition comprises HPV VLPs of at least HPV types 16 and 18.

In embodiment 14, the pharmaceutical composition of embodiments 12-13 is provided, wherein the pharmaceutical composition comprises HPV VLPs of at least HPV types 6, 11, 16, and 18.

In embodiment 15, the pharmaceutical composition of embodiments 12-14 is provided, wherein the pharmaceutical composition comprises HPV VLPs of at least HPV types 31, 45, 52, and 58.

In embodiment 16, the pharmaceutical composition of embodiments 12-15 is provided, wherein the pharmaceutical composition comprises HPV VLPs of at least HPV types 6, 11, 16, 18, 31, 33, 45, 52, and 58.

In embodiment 17, the pharmaceutical composition of embodiments 12-16 is provided, wherein the LNP adjuvant comprises a cationic lipid, a phospholipid, cholesterol, and a PEG-lipid.

In embodiment 18, the pharmaceutical composition of embodiments 12-17 is provided, wherein the LNP adjuvant comprises 30-65 mole % cationic lipid, 5-30 mole % phospholipid, 10-40 mole % cholesterol, and 0.5-4 mole % PEG-lipid.

In embodiment 19, the pharmaceutical composition of embodiments 12-18 is provided, wherein the LNP adjuvant comprises DSPC, cholesterol, ePEG2000-DMG, and (13Z, 16Z)-N, N-dimethyl-3-nonyldocosa 13, 16-dien-1-amine.

In embodiment 20, the pharmaceutical composition of embodiments 12-19 is provided, wherein the LNP adjuvant comprises 5-15 mole % DSPC, 25-35 mole % cholesterol, 1-2.5 mole % ePEG2000-DMG, and 55-65 mole % (13Z, 16Z)-N, N-dimethyl-3-nonyldocosa 13, 16-dien-1-amine.

In embodiment 20a, the pharmaceutical composition of embodiments 12-20 is provided, wherein the LNP adjuvant comprises 10 mole % DSPC, 30 mole % cholesterol, 2 mole % polymer lipid conjugate, and 58 mole % (13Z, 16Z)-N, N-dimethyl-3-nonyldocosa 13, 16-dien-1-amine.

In embodiment 20b, the pharmaceutical composition of embodiments 12-20 is provided, wherein the LNP adjuvant comprises 10 mole % DSPC, 30 mole % cholesterol, 2 mole % ePEG2000-DMG, and 58 mole % (13Z, 16Z)-N, N-dimethyl-3-nonyldocosa 13, 16-dien-1-amine.

In embodiment 20c, the pharmaceutical composition of embodiments 12-20 is provided, wherein the LNP adjuvant comprises 10 mole % DSPC, 30 mole % cholesterol, 2 mole % cPEG2000-DMG, and 58 mole % (13Z, 16Z)-N, N-dimethyl-3-nonyldocosa 13, 16-dien-1-amine.

In embodiment 20d, the pharmaceutical composition of embodiments 12-20 is provided, wherein the LNP adjuvant comprises 10 mole % DSPC, 30 mole % cholesterol, 2 mole % cPEG2000-DMG(s), and 58 mole % (13Z, 16Z)-N, N-dimethyl-3-nonyldocosa 13, 16-dien-1-amine.

In embodiment 21, the pharmaceutical composition of embodiments 12-20 and 20a-20d is provided, wherein the HPV VLPs comprise HPV L1 protein and do not comprise HPV L2 protein.

In embodiment 22, the pharmaceutical composition of embodiments 12-20 and 20a-20d is provided, wherein the HPV VLPs consists of the HPV L1 protein.

In embodiment 23, a single-dose vaccine composition is provided comprising:

a lipid nanoparticle (LNP) adjuvant, wherein the adjuvant comprises 30-65 mole % cationic lipid, 5-30 mole % phospholipid, 10-40% cholesterol, and 0.5-4 mole % PEG-lipid, virus-like particles (VLPs) at least one type of human papillomavirus (HPV) (HPV VLPs) selected from the group consisting of HPV types: 6, 11, 16, 18, 26, 31, 33, 35, 39, 45, 51, 52, 53, 55, 56, 58, 59, 66, 68, 73, and 82, wherein the single-dose vaccine composition provides an elevated or comparable anti-HPV immune response than relative to multiple doses of the same composition formulated, or administered, without an LNP adjuvant.

In embodiment 24, the single-dose vaccine composition of embodiment 23 is provided, wherein the HPV vaccine further comprises an aluminum adjuvant.

In embodiment 25, the single-dose vaccine composition of embodiment 24 is provided, wherein the HPV VLPs are adsorbed onto the aluminum adjuvant.

In embodiment 26, the single-dose vaccine composition embodiments 23-25 is provided, wherein each of the HPV VLPs, when present in the single-dose vaccine composition, are present in a concentration of about 10 μg to about 100 μg per 0.5 mL of the pharmaceutical composition and wherein the total HPV VLP concentration is between 10 μg and 2000 μg per 0.5 mL of the pharmaceutical composition.

In embodiment 26a, the single-dose vaccine composition of embodiments 23-26 is provided, wherein the single-dose vaccine composition comprises HPV VLPs of at least HPV types 16 and 18.

In embodiment 26b, the single-dose vaccine composition of embodiments 23-26 is provided, wherein the single-dose vaccine composition comprises HPV VLPs of at least HPV types 6, 11, 16, and 18.

In embodiment 26c, the single-dose vaccine composition of embodiments 23-26 is provided, wherein the single-dose vaccine composition comprises HPV VLPs of at least HPV types 31, 45, 52, and 58.

In embodiment 26d, the single-dose vaccine composition of embodiments 23-26 is provided, wherein the single-dose vaccine composition comprises HPV VLPs of at least HPV types 6, 11, 16, 18, 31, 33, 45, 52, and 58.

In embodiment 26e, the single-dose vaccine composition of embodiments 23-26d is provided, wherein the HPV VLPs comprise HPV L1 protein and do not comprise HPV L2 protein.

In embodiment 26f, the pharmaceutical composition of embodiments 23-26d is provided, wherein the HPV VLPs consists of the HPV L1 protein.

In embodiment 27, a method of inducing an immune response to a human papillomavirus (HPV) in a human patient is provided comprising administering to the patient the pharmaceutical composition of embodiments 1-22 or the single-dose vaccine composition of embodiments 23-26f.

In embodiment 28, a method of inducing an immune response to a human papillomavirus (HPV) in a human patient is provided comprising co-administering to the patient (a) a pharmaceutical composition comprising virus-like particles (VLPs) of at least one type of human papillomavirus (HPV) (HPV VLPs) selected from the group consisting of HPV types: 6, 11, 16, 18, 26, 31, 33, 35, 39, 45, 51, 52, 53, 55, 56, 58, 59, 66, 68, 73, and 82 and (b) an LNP adjuvant.

In embodiment 28a, the method of embodiment 28 is provided, wherein the pharmaceutical composition comprises HPV VLPs of at least HPV types 16 and 18.

In embodiment 28b, the method of embodiment 28 is provided, wherein the pharmaceutical composition comprises HPV VLPs of at least HPV types 6, 11, 16, and 18.

In embodiment 28c, the method of embodiment 28 is provided, wherein the pharmaceutical composition comprises HPV VLPs of at least HPV types 31, 45, 52, and 58.

In embodiment 28d, the method of embodiment 28 is provided, wherein the pharmaceutical composition comprises HPV VLPs of at least HPV types 6, 11, 16, 18, 31, 33, 45, 52, and 58.

In embodiment 28e, the method of embodiment 28 and 28a-28d is provided, wherein the pharmaceutical composition comprising HPV VLPs is an HPV vaccine.

In embodiment 28f, the method of embodiment 28e is provided, wherein the HPV vaccine is a Human Papillomavirus 9-valent Vaccine, Recombinant.

In embodiment 28 g, the method of embodiment 28e and 28f is provided, wherein the HPV vaccine is GARDASIL® 9.

In embodiment 29, a method of preventing infection of a human patient by a human papillomavirus (HPV) is provided comprising administration to the patient the pharmaceutical composition of embodiments 1-22 or the single-dose vaccine composition of embodiments 23 and 26f.

In embodiment 30, a method of preventing infection of a human patient by a human papillomavirus (HPV) is provided comprising co-administering to the patient (a) a pharmaceutical composition comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and (b) an LNP adjuvant.

In embodiment 30a, the method of embodiment 30 is provided, wherein the pharmaceutical composition comprises HPV VLPs of at least HPV types 16 and 18.

In embodiment 30b, the method of embodiment 30 is provided, wherein the pharmaceutical composition comprises HPV VLPs of at least HPV types 6, 11, 16, and 18.

In embodiment 30c, the method of embodiment 30 is provided, wherein the pharmaceutical composition comprises HPV VLPs of at least HPV types 31, 45, 52, and 58.

In embodiment 30d, the method of embodiment 30 is provided, wherein the pharmaceutical composition comprises HPV VLPs of at least HPV types 6, 11, 16, 18, 31, 33, 45, 52, and 58.

In embodiment 30e, the method of embodiment 30 and 30a-30d is provided, wherein the pharmaceutical composition comprising HPV VLPs is an HPV vaccine.

In embodiment 30f, the method of embodiment 30e is provided, wherein the HPV vaccine is a Human Papillomavirus 9-valent Vaccine, Recombinant.

In embodiment 30 g, the method of embodiment 30e and 30f is provided, wherein the HPV vaccine is GARDASIL® 9.

In embodiment 31, a kit is provided comprising (a) a human papilloma virus (HPV) vaccine; and (b) an LNP adjuvant.

In embodiment 32, the kit of embodiment 31 is provided further comprising instructions for co-administering to a human patient the HPV vaccine and the LNP adjuvant.

In embodiment 32a, the kit of embodiment 31 is provided further comprising instructions for admixing the HPV vaccine and the LNP adjuvant and administering the admixture to a human patient.

In embodiment 33, the kit of embodiments 31-32a is provided, wherein the HPV vaccine comprises virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82.

In embodiment 33a, the kit of embodiments 31-33 is provided, wherein the HPV vaccine is a Human Papillomavirus 9-valent Vaccine, Recombinant.

In embodiment 33b, the kit of embodiments 31-33a is provided, wherein the HPV vaccine is GARDASIL® 9.

In embodiment 34, a method of delivering a pharmaceutical composition that induces a neutralizing titer against an antigen in a host is provided comprising:

(a) administering a single-dose vaccine composition comprising:
  a lipid nanoparticle (LNP) adjuvant, and
  virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82,
  and
(b) inducing a neutralizing titer against an antigen in the host,
  where the single-dose vaccine composition provides enhanced or comparable neutralizing titers relative to multiple doses of the same composition formulated, or administered, without an LNP adjuvant.

In embodiment 35, the method of embodiment 34 is provided, further comprising an aluminum adjuvant.

In embodiment 36, a pharmaceutical composition is provided comprising (a) virus-like particles (VLPs) of HPV (HPV VLPs) types 6, 11, 16, 18, 31, 33, 45, 52, and 58:
(b) an LNP adjuvant:
(c) optionally an aluminum adjuvant; and
(d) a pharmaceutically acceptable carrier.

In embodiment 37, the pharmaceutical composition of embodiment 37 is provided, wherein the HPV VLPs comprise 30 μg of HPV VLPs of HPV Type 6 L1 protein, 40 μg of HPV VLPs of HPV Type 11 L1 protein, 60 μg of HPV VLPs of HPV Type 16 L1 protein, 40 μg of HPV VLPs of HPV Type 18 L1 protein, 20 μg of HPV VLPs of HPV Type 31 L1 protein, 20 μg of HPV VLPs of HPV Type 33 L1 protein, 20 μg of HPV VLPs of HPV Type 45 L1 protein, 20 μg of HPV VLPs of HPV Type 52 L1 protein, and 20 μg of HPV VLPs of HPV Type 58 L1 protein.

In embodiment 38, the pharmaceutical composition of embodiments 36-37 is provided, wherein the LNP adjuvant comprises about 1 μg to about 200 mg of LNP adjuvant.

In embodiment 39, the pharmaceutical composition of embodiments 36-38 is provided, wherein the pharmaceutical composition comprises about 100 μg to about 900 μg of aluminum adjuvant.

In embodiment 39a, the pharmaceutical composition of embodiment 39 is provided, wherein the HPV VLPs are adsorbed onto the aluminum adjuvant.

In embodiment 40, the pharmaceutical composition of embodiments 36-39 is provided, wherein the LNP adjuvant comprises a cationic lipid, a phospholipid, cholesterol, and a PEG-lipid.

In embodiment 41, the pharmaceutical composition of embodiments 36-40 is provided, wherein the LNP adjuvant comprises 30-65 mole % cationic lipid, 5-30 mole % phospholipid, 10-40% cholesterol, and 0.5-4 mole % PEG-lipid.

In embodiment 42, the pharmaceutical composition of embodiments 36-41 is provided, wherein the LNP adjuvant comprises DSPC, cholesterol, ePEG2000-DMG, and (13Z, 16Z)-N, N-dimethyl-3-nonyldocosa 13, 16-dien-1-amine.

In embodiment 43, the pharmaceutical composition of embodiments 36-42 is provided, wherein the LNP adjuvant comprises 5-15 mole % DSPC, 25-35 mole % cholesterol, 1-2.5 mole % ePEG2000-DMG, and 55-65 mole % (13Z, 16Z)-N, N-dimethyl-3-nonyldocosa 13, 16-dien-1-amine.

In embodiment 44, the pharmaceutical composition of embodiments 36-43 is provided wherein the LNP adjuvant comprises 10 mole % DSPC, 30 mole % cholesterol, 2 mole % ePEG2000-DMG, and 58 mole % (13Z, 16Z)-N, N-dimethyl-3-nonyldocosa 13, 16-dien-1-amine.

In embodiment 45, a method of inducing an immune response to a human papillomavirus (HPV) in a human patient is provided comprising administering to the patient the pharmaceutical composition of embodiments 36-44.

In embodiment 46, a method of preventing infection of a human patient by a human papillomavirus (HPV) is provided comprising administration to the patient the pharmaceutical composition of embodiments 36-44.

All publications mentioned herein are incorporated by-reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be used by one skilled in the art without departing from the scope or spirit of the invention as defined in the appended claims.

The following examples illustrate, but do not limit the invention.

EXAMPLES

Example 1: Preparation of Lipid Nanoparticle Adjuvant

Compositions that include an LNP adjuvant of the present invention were made according to the following method. First, the lipid components (DSPC, cholesterol, ePEG2000-DMG, and (13Z, 16Z)-N, N-dimethyl-3-nonyldocosa 13, 16-dien-1-amine) were dissolved in ethanol to form an organic solution. The lipid/ethanol composition was then exposed to a rapid precipitation process, whereby the lipid/ethanol solution was micro-mixed with an aqueous solution of a sodium citrate buffered salt solution having a pH of about 2-6 using a confined volume T-mixer apparatus. The aqueous and organic solutions were combined in a confined-volume mixer with a ratio in the range of about 1:1 to 4:1 vol: vol, with a total flow rate from 10 mL/min-600 L/minute, to form the LNP adjuvant. The resulting LNP adjuvant was diluted with a citrate buffer having a pH of about 6-8.

The LNP adjuvant was then concentrated and filtered via an ultrafiltration process where the alcohol was removed, and the buffer was exchanged for phosphate buffered saline having a pH between 6-8. The ultrafiltration process, having a tangential flow filtration format ("TFF"), used a hollow fiber membrane nominal molecular weight cutoff range from 30-500 KD, targeting 100 KD. The TFF retained the LNP in the retentate and the filtrate or permeate contained the alcohol and final buffer wastes. The TFF provided an initial LNP concentration to a lipid concentration of 1-100 mg/mL. Following concentration, the LNP adjuvant was diafiltered against the final buffer (for example, phosphate buffered saline ("PBS") to remove the alcohol and perform buffer exchange. The material was then concentrated via ultrafiltration.

The concentrated LNP adjuvant was then sterile filtered into a suitable container under aseptic conditions. Sterile filtration was accomplished by passing the LNP suspension through a pre-filter (Acropak 500 PES 0.45/0.8 μη capsule) and a bioburden reduction filter (Acropak 500 PES 0.2/0.8 μη capsule). Following filtration, the vialed LNP adjuvant was stored under suitable conditions.

Example 2: Preparation of Inventive Compositions

A formulation including the LNP adjuvant described in Example 1 (hereinafter "LNP Adjuvant") was combined with a dose of a 9 valent HPV/aluminum adjuvant vaccine (hereinafter "9vHPV Vaccine") to make a single-dose vaccine composition.

Example 3: In Vivo Pharmacology

Following the initial immunogenicity screening in rabbits of several different adjuvants in combination with 9vHPV Vaccine, the studies described below were conducted to confirm the observation that a single-dose vaccine composition of 9vHPV Vaccine admixed with LNP Adjuvant resulted in immune responses comparable to those achieved following 2-doses of 9vHPV Vaccine.

Example 4. Immunogenicity and Durability of a Single Dose of 9vHPV Vaccine+LNP Adjuvant in Rabbits As described in Table 1 below; the immunogenicity of 9vHPV Vaccine when combined with the LNP Adjuvant was evaluated in a rabbit nonclinical immunogenicity model. In Group 1, four New Zealand white rabbits were vaccinated via IM administration with a single-dose (i.e. one dose, at week 0), of a 9vHPV Vaccine. In Group 2, four New Zealand white rabbits were vaccinated via IM with multi-dose (i.e. two doses, one at week ( ) and one at week 4), of a 9vHPV Vaccine. In Group 3, four New Zealand white rabbits were vaccinated with a single-dose (i.e. one dose, at week 0)), of a 9vHPV Vaccine admixed with LNP Adjuvant. The latter consisted of 0.5 mL inoculums prepared by mixing 9vHPV Vaccine with LNP Adjuvant and injecting into the rabbit hind quadricep via IM administration within 4 hours.

TABLE 1

Groups, Dose Levels, and Dosing Schedule in Rabbits

| | | | Dose level | | | |
|---|---|---|---|---|---|---|
| Group | No. of rabbits | Inoculum | 9vHPV Vaccine[b] | LNP Adjuvant[c] | ROA[a] | Dosing schedule |
| 1 | 4 | 9vHPV Vaccine | One dose[b] | NA | IM | week 0 |
| 2 | 4 | 9vHPV Vaccine | | NA | IM | 0, 4 weeks |
| 3 | 4 | 9vHPV Vaccine + LNP Adjuvant | | 1 mg | IM | week 0 |

[a]All doses were delivered in 500 μL to a single quadricep
[b]One rabbit dose of 9vHPV Vaccine is equivalent to 1/20 of one human dose of 9vHPV Vaccine.
[c]The dose of LNP Adjuvant refers to the total lipid dose
IM = intramuscular; NA = not applicable; ROA = route of administration To assess immunogenicity, sera from individual animals were evaluated using a multiplex assay to measure antibody levels to the 9 HPV types in the vaccine. HPV VLP antibody concentrations were determined at study week 4, 6 12, 24, 36 and 48. Representative titers to HPV VLP 16 and HPV VLP 18 are shown in FIG. 1. Group 3, i.e. the animals that received a single-dose (i.e. a single inoculation) of a 9vHPV Vaccine combined with LNP Adjuvant, produced similar antibody concentrations to Group 2, i.e. animals that received multi-dose (i.e. two doses) of a 9vHPV Vaccine injected 4 weeks apart. Antibody levels for Group 3, i.e. the animals that received a 9vHPV Vaccine mixed with LNP Adjuvant, were approximately 10 times higher compared to those of Group 1, i.e. animals receiving a single-dose of only a 9vHPV Vaccine. Antibody levels for Group 3, i.e. those that received a 9vHPV Vaccine+LNP Adjuvant, remained at similar levels throughout the duration of the study (48 weeks).

Figure 1B:
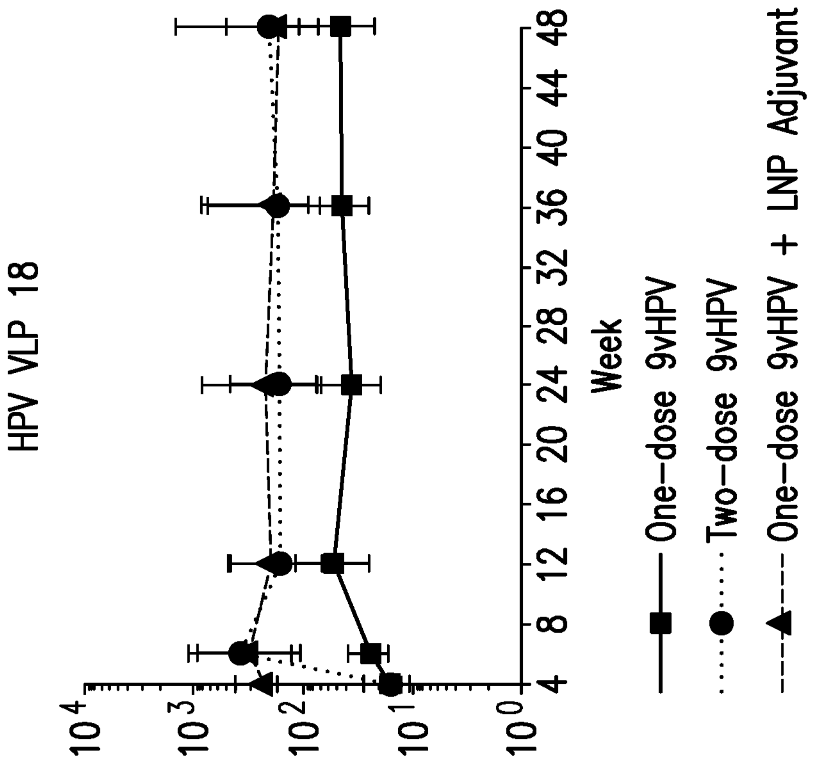

Rabbits (n=4/group) were injected intramuscularly with a single-dose regimen (i.e. one dose administered only at week 0) or a multi-dose regimen (i.e. one does administered at week 0 and a second dose administered at week 4) doses of 9vHPV Vaccine (9vHPV) and compared to a group that received a single-dose (i.e. one dose administered at week 0) of 9vHPV Vaccine admixed with 1 mg LNP Adjuvant. Antibody (Ab) levels against all 9 human papillomavirus (HPV) virus like particle (VLP) types were monitored for 48 weeks. FIG. 1 depicts the antibody concentrations (μg/mL) detected in serum against HPV VLP type 16 (FIG. 1A) and 18 (FIG. 1B) at weeks 4, 6, 12, 24, 36, and 48. The data are presented as geometric mean concentrations and 95% confidence intervals (CI). Immune responses observed for all 9

Figure 2:
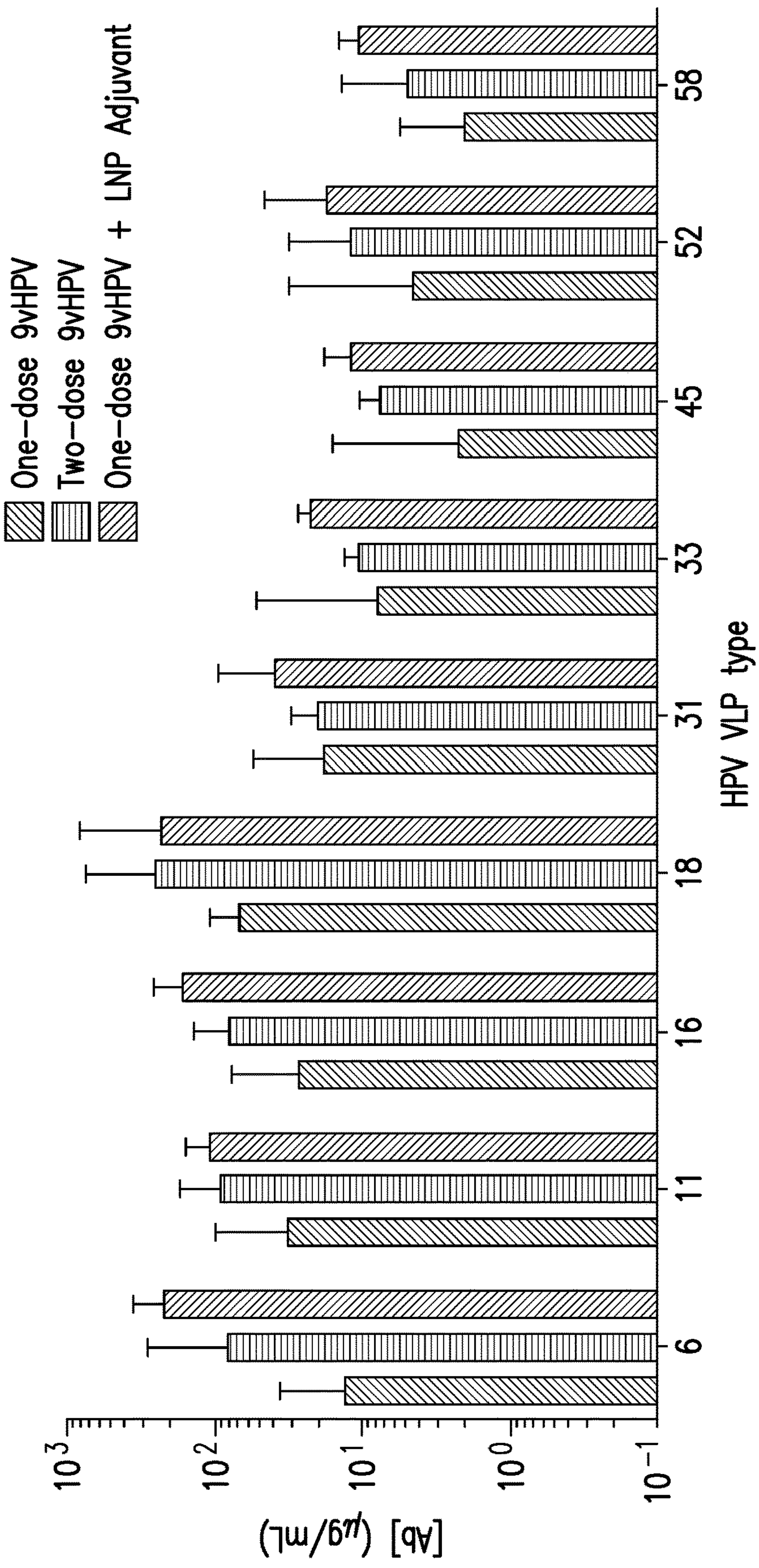
FIG. 2 shows individual HPV VLP antibody levels in rabbits measured at 48 weeks after a single inoculation of a 9 valent HPV vaccine combined with an LNP adjuvant.

VLP types at week 48 are presented in FIG. 2. Anti-HPV VLP antibody levels were similar to or higher in Group 3 than Group 2 for all types.

Rabbits (n=4/group) were injected intramuscularly with a single-dose regimen (i.e. one dose administered at week 0) or a multi-dose regimen (i.e. one dose administered at week 0 and a second dose administered at week 4) of 9vHPV Vaccine (9vHPV)) and compared to a group that received a single-dose (i.e. one dose administered at week 0) of 9vHPV Vaccine admixed with 1 mg LNP adjuvant. Antibody (Ab) levels against all 9 HPV virus like particle (VLP) types were monitored for 48 weeks. Shown are the Ab concentrations (μg/mL) detected in serum against the nine HPV VLP types at week 48. The data are presented as geometric mean concentrations and 95% confidence intervals (CI).

Example 5: Immunogenicity and Durability of a Single Dose of 9vHPV Vaccine+LNP Adjuvant in Rhesus Macaques The immunogenicity of 9vHPV Vaccine when combined with increasing the quantity or amount of LNP Adjuvant was evaluated in a non-human primate nonclinical immunogenicity model. The group designations are described in Table 2. In Groups 1, 3, 4, and 5, 6 rhesus macaques were inoculated at week 0 with either a single-dose of 9vHPV Vaccine alone or with 9vHPV Vaccine combined with 1, 3, or 6 mg of LNP Adjuvant. In Group 2, 6 rhesus macaques were inoculated with a multi-dose regimen, where the animals were given a first dose of 9vHPV vaccine at week 0 and a second dose of 9vHPV vaccine at week 4. The 1.0-mL doses of the 9vHPV Vaccine combined with 1, 3, or 6 mg of LNP Adjuvant were prepared by mixing the 9vHPV Vaccine and the LNP Adjuvant and administering the combination into the rhesus macaque quadricep within 4 hours of formulation.

TABLE 2

Groups, Dose Levels, and Dosing Schedule in Non-human Primates

| Group | No. of rhesus macaques | Inoculum | Dose level: 9vHPV Vaccine[b] | Dose level: LNP Adjuvant[c] | ROA[a] | Dosing schedule |
|---|---|---|---|---|---|---|
| 1 | 6 | 9vHPV Vaccine | One dose[b] | NA | IM | week 0 |
| 2 | 6 | 9vHPV Vaccine | | NA | IM | 0, 4 weeks |
| 3 | 6 | 9vHPV Vaccine + LNP Adjuvant | | 1 mg | IM | week 0 |
| 4 | 6 | 9vHPV Vaccine + LNP Adjuvant | | 3 mg | IM | week 0 |
| 5 | 6 | 9vHPV Vaccine + LNP Adjuvant | | 6 mg | IM | week 0 |

[a] All doses were delivered in 1 mL to single quadricep

[b]One rhesus monkey dose of 9vHPV Vaccine is equivalent to 1/20 of one human dose of 9vHPV vaccine.

[c]The dose of LNP Adjuvant refers to the total lipid dose

IM = intramuscular; NA = not applicable; ROA = route of administration

Figure 3A:
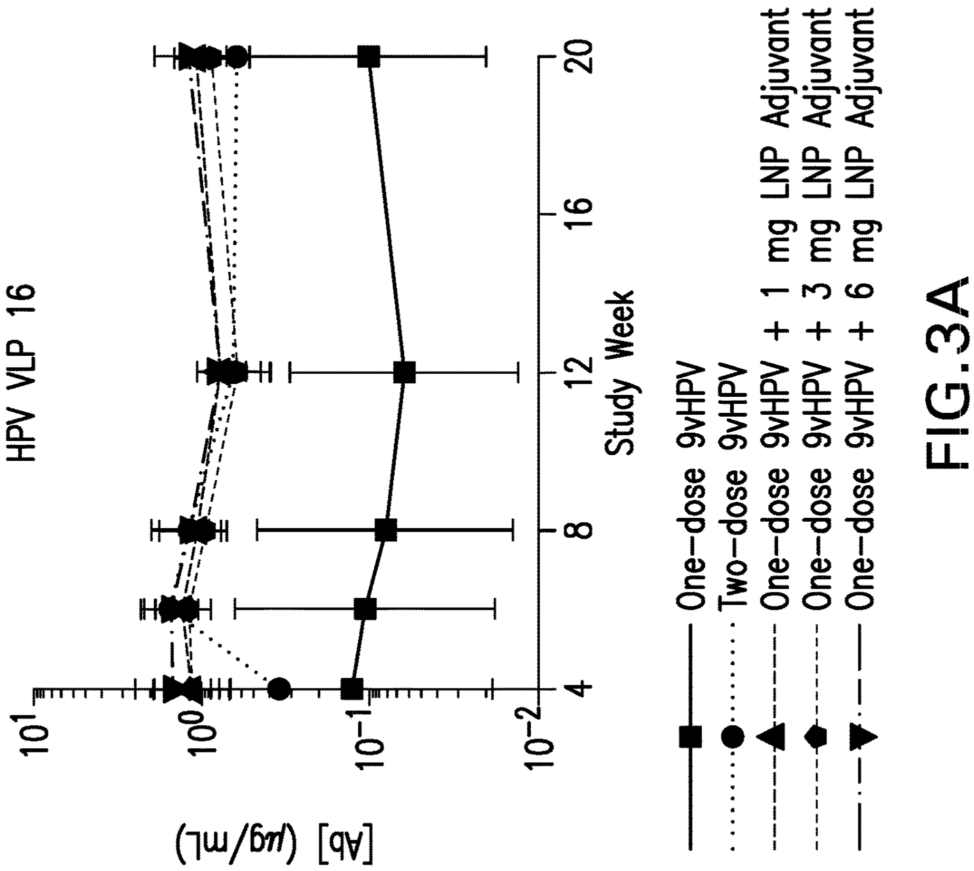
FIGS. 3A and 3B show longitudinal HPV VLP 16 (FIG. 3A) and HPV VLP 18 (FIG. 3B) antibody levels in rhesus macaques after a single inoculation of a 9 valent HPV vaccine combined with an LNP adjuvant.
Figure 3B:
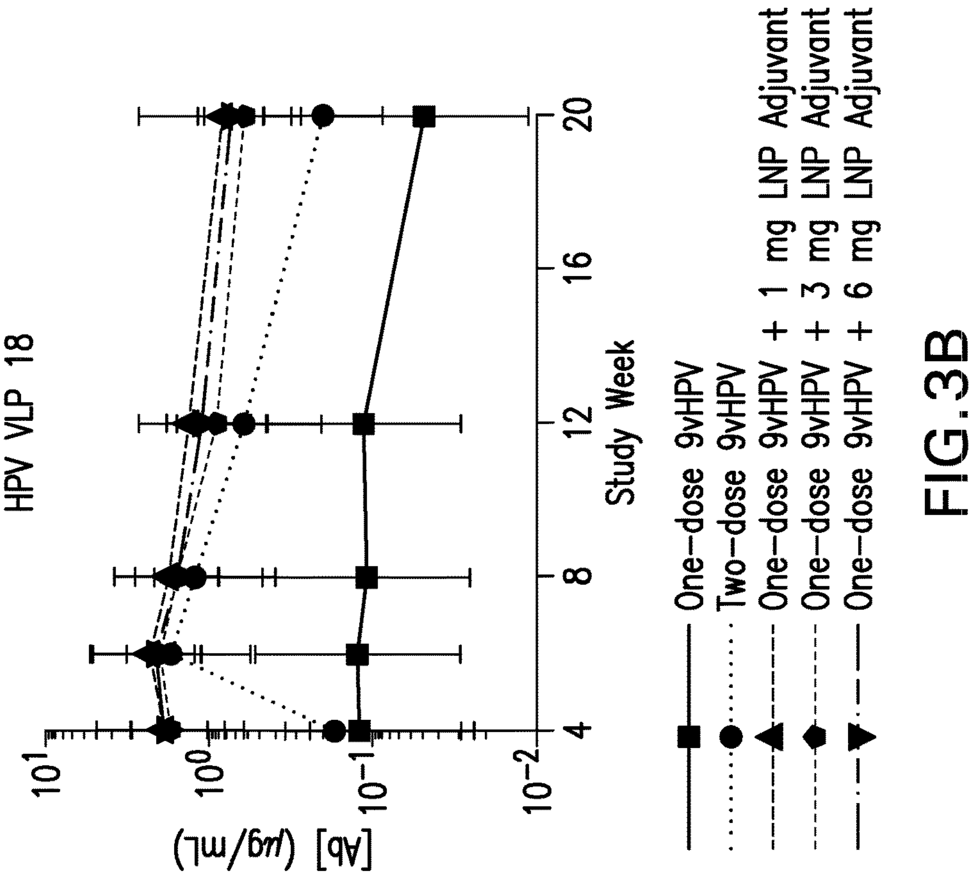
Figure 4:
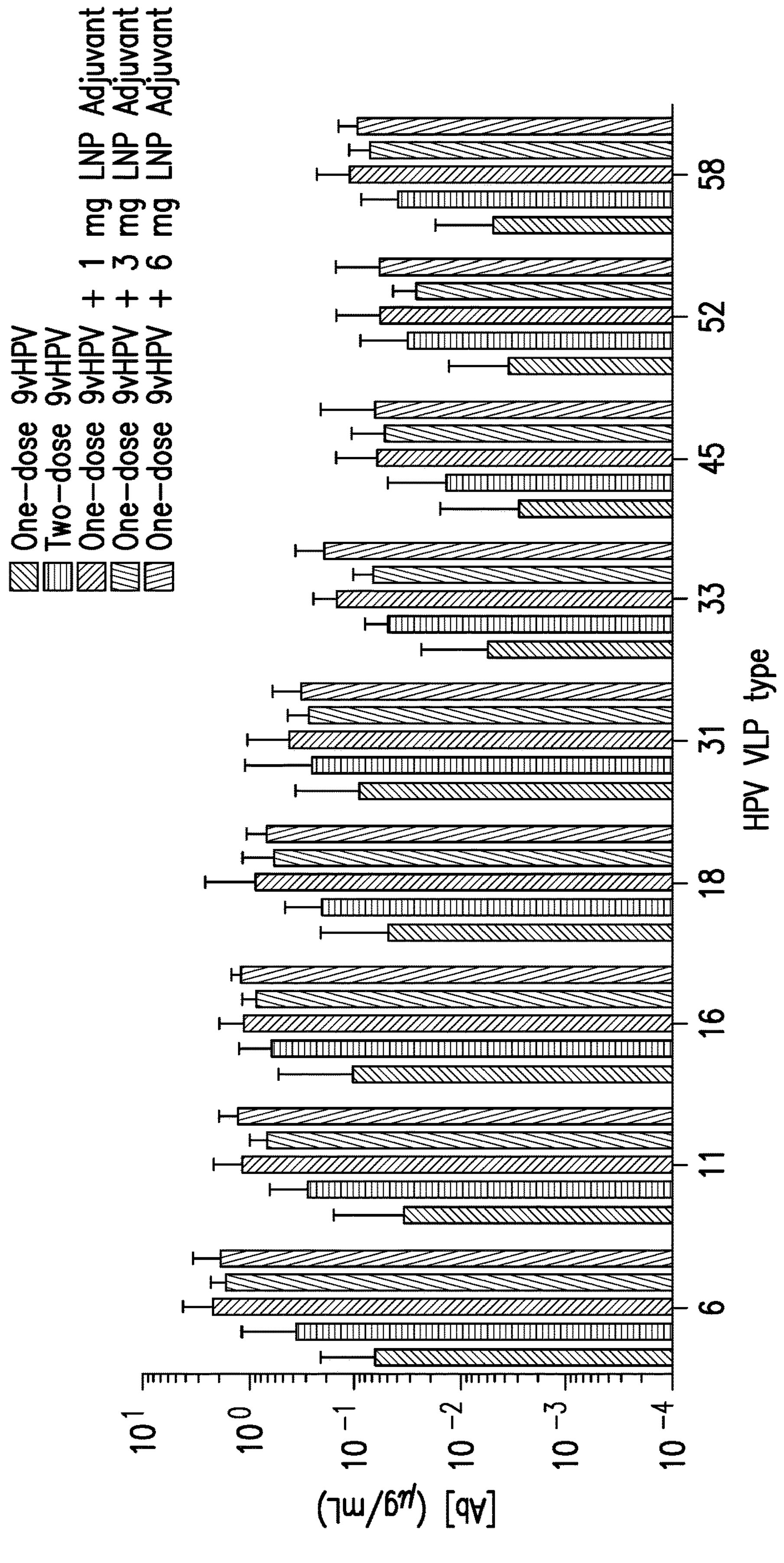
FIG. 4 shows individual HPV VLP antibody levels in rhesus macaques measured at 20 weeks after a single inoculation of a 9 valent HPV vaccine combined with an LNP adjuvant.

Rhesus macaques (n=6/group) were injected intramuscularly with one (week 0) or two (week 0 and week 4) doses of 9vHPV Vaccine (9vHPV) or one dose (week 0) of 9vHPV Vaccine combined with 1, 3, or 6 mg of LNP Adjuvant. Antibody (Ab) levels against all 9 HPV VLP types were monitored for 20 weeks. FIG. 3 shows the antibody concentrations (μg/mL) detected in serum against HPV VLP type 16 (FIG. 3A) and 18 (FIG. 3B) at weeks 4, 6, 8, 12, and 20. FIG. 4 shows the antibody concentrations (μg/mL) detected in serum against the nine HPV VLP types at week 20. The data from both figures are presented as geometric mean concentrations and 95% confidence intervals (CI).

To assess immunogenicity, sera from individual animals were evaluated using a multiplex assay to measure antibody levels to the 9 HPV types in the vaccine. HPV VLP antibody concentrations were determined at study week 4, 6, 8 12, and 20. As shown in FIGS. 3 and 4, a single inoculation of 9vHPV Vaccine combined with LNP Adjuvant produced similar antibody concentrations to two doses of 9vHPV Vaccine injected 4 weeks apart at all dose levels of LNP Adjuvant evaluated. A single-dose regimen (i.e. single inoculation) of 9vHPV Vaccine combined with LNP Adjuvant produced similar antibody concentrations to a multi-dose regimen (i.e. two separate doses) of 9vHPV Vaccine injected 4 weeks apart. Antibody levels in the single-dose 9vHPV Vaccine+LNP Adjuvant group remained at similar levels out to 20 weeks post vaccination. In the animals that received 9vHPV Vaccine combined with LNP Adjuvant, anti-HPV VLP antibody levels were similar to or higher than the multi-dose 9vHPV Vaccine group for all types.

Example 6: Immunogenicity of a Single Dose of 9vHPV Vaccine Combined with Lower Dose Levels of LNP Adjuvant in Rhesus Macaques The immunogenicity of the 9vHPV Vaccine when combined with lower quantities of LNP Adjuvant (1 mg, 0.33 mg, and 0.11 mg) was evaluated in a non-human primate nonclinical immunogenicity model. The group designations are described in Table 3 below. At week 0, each group was inoculated with either 9vHPV Vaccine alone or with 9vHPV Vaccine combined with 1 mg, 0.33 mg, or 0.11 mg of LNP Adjuvant. At week 4, the animals in Group 2 were given a second dose of 9vHPV Vaccine. No other groups were boosted. The 1.0-mL doses were prepared by mixing 9vHPV Vaccine and LNP Adjuvant and administering into the Rhesus macaque quadricep within 4 hours.

TABLE 3

Groups, Dose Levels, and Dosing Schedule in Non-human Primates

| Group | No. of rhesus macaques | Inoculum | Dose level 9vHPV Vaccine[b] | Dose level LNP Adjuvant[c] | ROA[a] | Dosing schedule |
|---|---|---|---|---|---|---|
| 1 | 5 | 9vHPV Vaccine | One dose | NA | IM | 0, 4 weeks |
| 2 | 5 | 9vHPV Vaccine + LNP Adjuvant | | 1 mg | IM | Week 0 |
| 3 | 5 | 9vHPV Vaccine + LNP Adjuvant | One dose | 0.33 mg | IM | Week 0 |
| 4 | 5 | 9vHPV Vaccine + LNP Adjuvant | | 0.11 mg | IM | Week 0 |

[a]All doses were delivered in 1 mL to single quadricep

[b]One rhesus monkey dose of 9vHPV Vaccine is equivalent to 1/20 of one human dose of 9vHPV Vaccine.

[c]The dose of LNP Adjuvant refers to the total lipid dose

IM = intramuscular; NA = not applicable; ROA = route of administration

To assess immunogenicity, sera from individual animals were evaluated using a multiplex assay to measure antibody levels to the 9 HPV types of the 9 valent HPV vaccine. HPV VLP antibody concentrations were determined at weeks 4, 6, and 12. Representative titers to HPV VLP 16 and HPV VLP 18 are shown in FIG. 5. The antibody levels measured in the animals that received a single-dose (i.e. single inoculation) of 9vHPV Vaccine combined with LNP Adjuvant were dependent on the quantity or dose of LNP Adjuvant administered. Animals that received 9vHPV Vaccine combined with 1 mg of LNP Adjuvant had similar antibody concentrations to animals that received a multi-dose regimen (i.e. two doses of 9vHPV Vaccine) injected 4 weeks apart. Animals that received 9vHPV Vaccine combined with a 0.33 or 0.11 mg dose of LNP Adjuvant had lower antibody concentrations than the groups that received a 1 mg of LNP Adjuvant and a multi-dose regimen (i.e. two doses of 9vHPV Vaccine). It is noted that the antibody levels measured in the animals receiving a single-dose of 9vHPV Vaccine combined with the 0.11 mg of LNP Adjuvant were similar to animals that received a single-dose of 9vHPV Vaccine alone. i.e. were administered 9vHPV Vaccine formulated without the LNP Adjuvant.

Figure 5B:
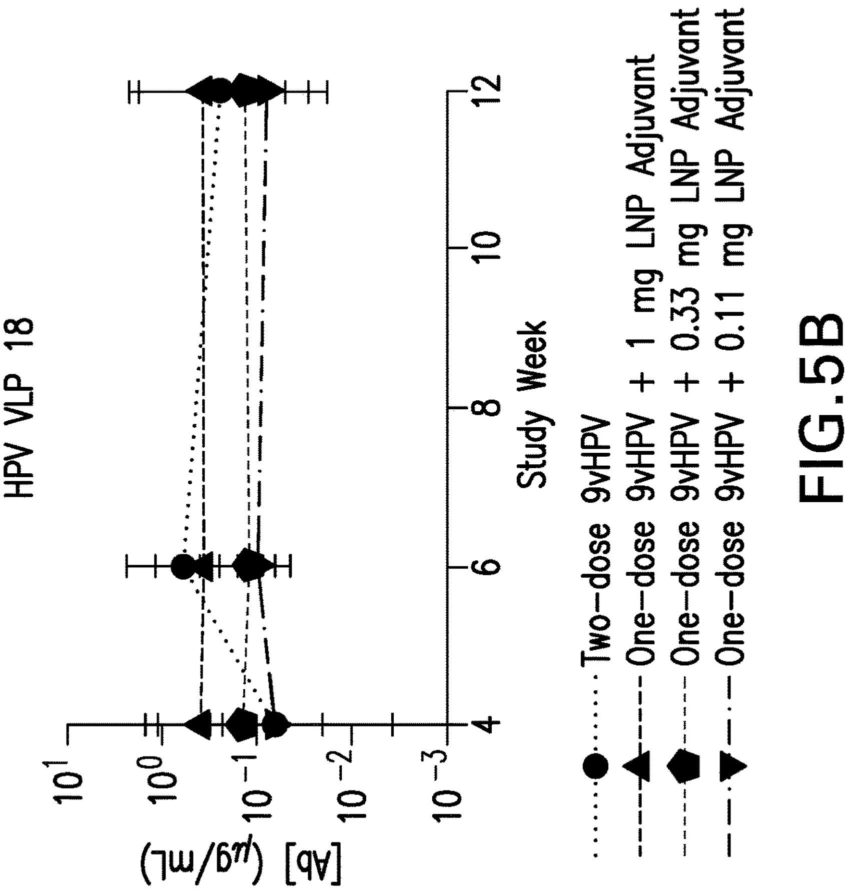
FIGS. 5A and 5B show longitudinal HPV VLP 16 (FIG. 5A) and HPV VLP 18 (FIG. 5B) antibody levels in rhesus macaques after a single inoculation of a 9 valent HPV vaccine combined with an LNP adjuvant.
Figure 5A:
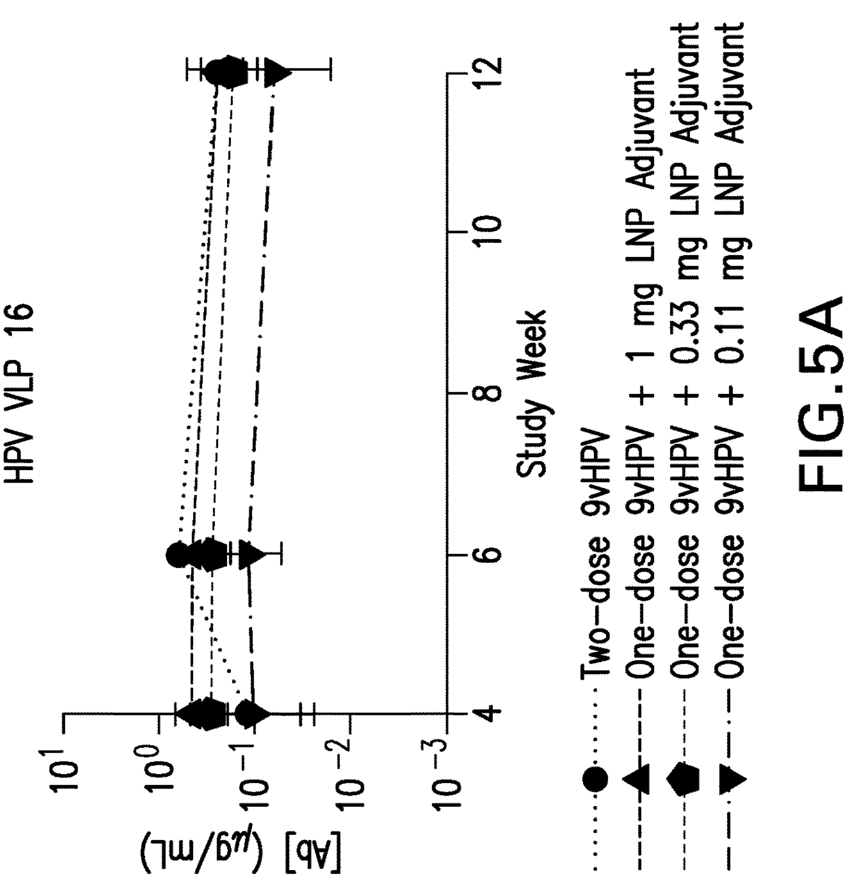
Figure 6:
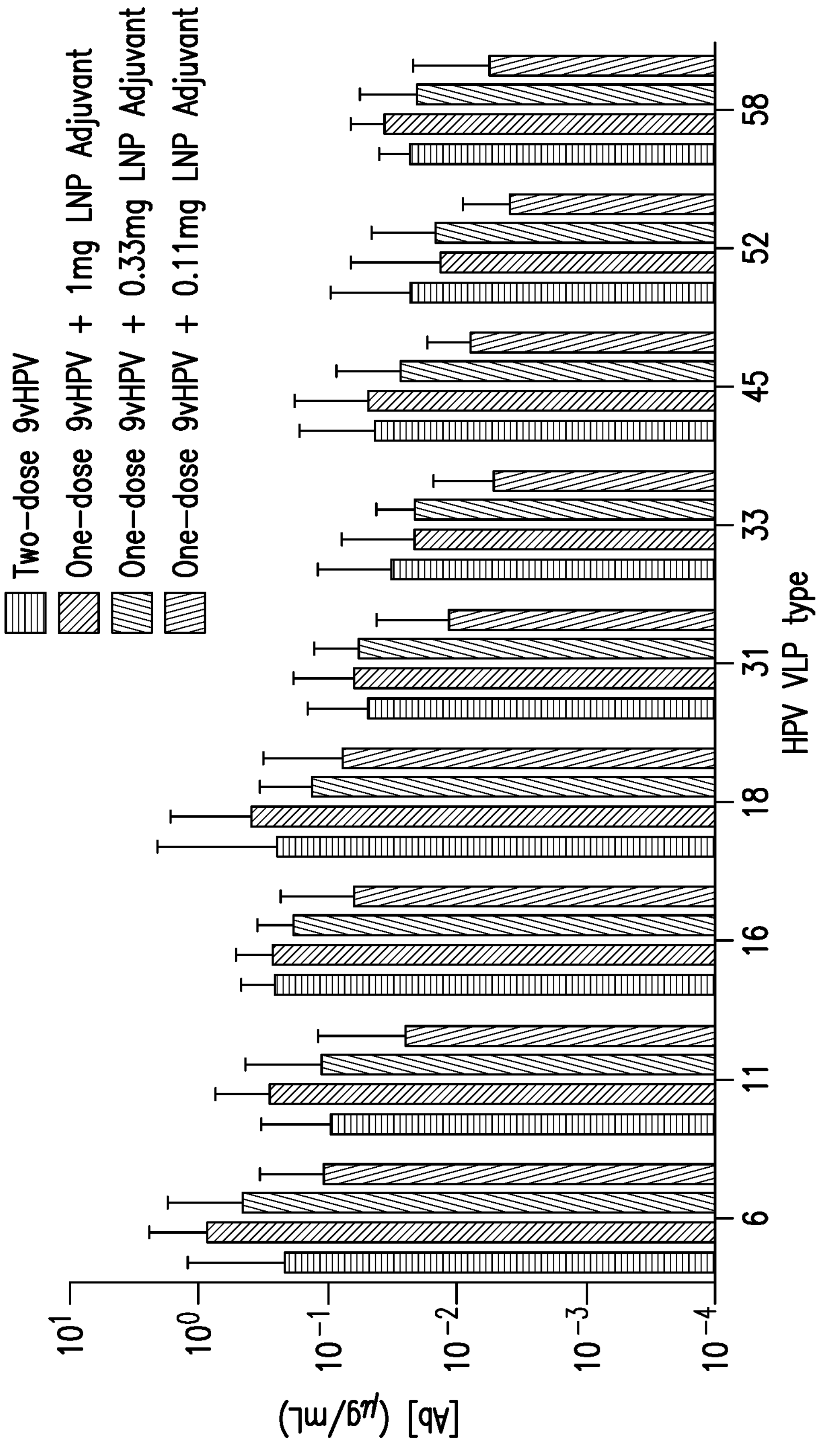
FIG. 6 shows individual HPV VLP antibody levels in rhesus macaques measured at 12 weeks after a single inoculation of a 9 valent HPV vaccine combined with an LNP adjuvant.

Rhesus macaques (n=5/group) were injected intramuscularly with two (week ( ) and week 4) doses of 9vHPV Vaccine or one dose (week 0) of 9vHPV Vaccine combined with 1.0.33. or 0.11 mg of LNP Adjuvant. Antibody (Ab) levels against all 9 human papillomavirus (HPV) virus like particle (VLP) types were monitored for 12 weeks. Shown in FIG. 5 are the antibody concentrations (μg/mL) detected in serum against HPV VLP type 16 (FIG. 5A) and 18 (FIG. 5B) at weeks 4, 6 and 12. Shown in FIG. 6 are the antibody concentrations (μg/mL) detected in serum against the nine HPV VLP types at week 12. The data in both figures are presented as geometric mean concentrations and 95% confidence intervals (CI).

Antibody levels in the 9vHPV Vaccine+LNP Adjuvant groups remained at similar levels out to 12 weeks post vaccination. Immune responses observed for all 9 VLP types at week 12 are presented in FIG. 6. The antibody levels measured in the animals that received a single-dose (i.e. single inoculation) of 9vHPV Vaccine combined with LNP Adjuvant were dependent on the dose or quantity of LNP Adjuvant administered. In the animals that received a single-dose of 9vHPV Vaccine combined with a 1 mg dose of LNP Adjuvant, anti-HPV VLP antibody levels were similar to or higher than the multi-dose 9vHPV Vaccine group for all types.

Example 7: Phase 1 Clinical Study to Evaluate the Safety and Tolerability of Single Dose Gardasil® 9 with an LNP Adjuvant The goal of the Phase 1 study is to assess the safety and tolerability of a 9 valent HPV vaccine (GARDASIL® 9) combined with the LNP adjuvant and to determine if ascending doses of the LNP adjuvant. when added to the 9 valent HPV vaccine, stimulate antibody responses to each HPV type that are comparable to those achieved with the approved 2-3 dose clinical regimen for GARDASIL®9. The study is a single dose escalation study with regard to the LNP Adjuvant. with up to four escalating panels of up to 16 healthy young adult subjects per panel. Each panel of subject will receive the components of GARDASIL® 9 (containing 270 μg of VLPs of 9 HPV types and 500 μg of AAHS) combined with a specific LNP Adjuvant dose per panel in a 1 ml IM injection. Each panel will be dosed and followed for safety and tolerability for up to 1 week before a dose escalation decision is made. HPV type specific IgG GMT (geometric mean titer) at 7, 12, 18 and 24 month timepoints will serve as the primary endpoint.

What is claimed:

1. A pharmaceutical composition comprising:

virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, a lipid nanoparticle (LNP) adjuvant, and a pharmaceutically acceptable carrier.

2. A pharmaceutical composition comprising:

(a) virus like particles (VLPs) of at least one type of human papillomavirus (HPV), wherein the at least one type of HPV is selected from the group consisting of HPV types: 6, 11, 16, 18, 26, 31, 33, 35, 39, 45, 51, 52, 53, 55, 56, 58, 59, 66, 68, 73, and 82;

(b) about 100 μg to about 900 μg of an aluminum adjuvant; and (c) about 10 μg to about 200 mg of a lipid nanoparticle (LNP) adjuvant, wherein each of the HPV VLPs comprise recombinant L1 or recombinant L1+L2 protein;

wherein each of the HPV VLPs are present in a concentration of about 10 μg to about 100 μg per 0.5 mL of the pharmaceutical composition;

wherein the total HPV VLP concentration is between 10 μg and 2000 μg per 0.5 mL of the pharmaceutical composition; and wherein the HPV VLPs are adsorbed onto the aluminum adjuvant.

3. The pharmaceutical composition of claim 2, wherein the pharmaceutical composition comprises HPV VLPs of at least HPV types 16 and 18.

4. The pharmaceutical composition of claim 2, wherein the pharmaceutical composition comprises HPV VLPs of at least HPV types 6, 11, 16, and 18.

5. The pharmaceutical composition of claim 2, wherein the pharmaceutical composition comprises HPV VLPs of at least HPV types 6, 11, 16, 18, 31, 33, 45, 52, and 58.

6. The pharmaceutical composition of claim 2, wherein the LNP adjuvant comprises 30-65 mole % cationic lipid, 5-30 mole % phospholipid, 10-40 mole % cholesterol, and 0.5-4 mole % polyethylene glycol lipid (PEG-lipid).

7. The pharmaceutical composition of claim 6, wherein the LNP adjuvant comprises 1,2-Distearoyl-sn-glycero-3-phosphocholine (DSPC), cholesterol, ePEG2000-DMG (dimyristolglycerol), and (13Z, 16Z)-N, N-dimethyl-3-nonyldocosa 13, 16-dien-1-amine.

8. The pharmaceutical composition of claim 7, wherein the LNP adjuvant comprises 5-15 mole % 1,2-Distearoyl-sn-glycero-3-phosphocholine (DSPC), 25-35 mole % cholesterol, 1-2.5 mole % ePEG2000-DMG (dimyristolglycerol), and 55-65 mole % (13Z, 16Z)-N, N-dimethyl-3-nonyldocosa 13, 16-dien-1-amine.

9. The pharmaceutical composition of claim 2, wherein the HPV VLPs comprise HPV L1 protein and do not comprise HPV L2 protein.

10. The pharmaceutical composition of claim 2, wherein the HPV VLPs consists of HPV L1 protein.

11. A method of inducing an immune response to a human papillomavirus (HPV) in a human patient comprising administering to the patient the pharmaceutical composition of claim 2.

12. A method of inducing an immune response to a human papillomavirus (HPV) in a human patient comprising co-administering to the patient (a) a pharmaceutical composition comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and (b) an LNP adjuvant.

13. A method of preventing infection of a human patient by a human papillomavirus (HPV) comprising administration to the patient the pharmaceutical composition of claim 2.

14. A method of preventing infection of a human patient by a human papillomavirus (HPV) comprising co-administering to the patient (a) a pharmaceutical composition comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82 and (b) an LNP adjuvant.

15. A kit comprising:

(a) a human papilloma virus (HPV) vaccine comprising virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82; and (b) an LNP adjuvant.

16. The kit of claim 15, further comprising instructions for administering to a human patient the HPV vaccine and the LNP adjuvant.

17. A method of delivering a pharmaceutical composition that induces a neutralizing titer against an HPV antigen in a host comprising:

(a) administering a pharmaceutical composition comprising:

a lipid nanoparticle (LNP) adjuvant, and virus-like particles (VLPs) of at least one type of human papillomavirus (HPV) selected from the group consisting of HPV types: 6, 11, 16, 18, 26, 31, 33, 35, 39, 45, 51, 52, 53, 55, 56, 58, 59, 66, 68, 73, and 82, and (b) inducing a neutralizing titer against the HPV antigen in the host, where a single dose of the pharmaceutical composition provides enhanced or comparable neutralizing titers when compared to multiple doses of the same pharmaceutical composition when the anti-HPV composition is formulated without an adjuvant.

* * * * *